US012606666B2

(12) United States Patent
Coates et al.

(10) Patent No.: US 12,606,666 B2
(45) Date of Patent: Apr. 21, 2026

(54) IMIDAZOLES AND IMIDAZOLIUM CATIONS WITH EXCEPTIONAL ALKALINE STABILITY

(71) Applicant: CORNELL UNIVERSITY, Ithaca, NY (US)

(72) Inventors: Geoffrey W. Coates, Lansing, NY (US); Kristina M. Hugar, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 1060 days.

(21) Appl. No.: 17/647,007

(22) Filed: Jan. 4, 2022

(65) Prior Publication Data

US 2022/0127413 A1 Apr. 28, 2022

Related U.S. Application Data

(62) Division of application No. 15/566,595, filed as application No. PCT/US2016/027543 on Apr. 14, 2016, now Pat. No. 11,242,432.

(Continued)

(51) Int. Cl.
*C08G 61/04* (2006.01)
*B01D 71/44* (2006.01)
(Continued)

(52) U.S. Cl.
CPC ............. *C08G 61/04* (2013.01); *B01D 71/44* (2013.01); *B01D 71/62* (2013.01); *C07D 233/58* (2013.01); *C07D 233/60* (2013.01); *C08F 8/30* (2013.01); *C08F 12/26* (2013.01); *C08F 210/14* (2013.01); *C08G 61/02* (2013.01); *C08G 61/06* (2013.01); *C08G 61/08* (2013.01); *C08L 25/18* (2013.01); *C08L 71/02* (2013.01); *H01M 8/1023* (2013.01); *H01M 50/414* (2021.01); *C08F 26/06* (2013.01); *C08F 126/06* (2013.01); *C08F 212/14* (2013.01); *C08F 212/36* (2013.01); *C08F 226/06* (2013.01); *C08G 2261/1424* (2013.01); *C08G 2261/148* (2013.01);
(Continued)

(58) Field of Classification Search
CPC ........ C08G 61/04; C08G 61/02; C08G 61/06; C08G 61/08; H01M 50/414; H01M 8/1023; B01D 71/44; B01D 71/62; C07D 233/58; C07D 233/60; C07F 8/80; C07F 12/26; C07F 210/14; C08L 215/18; C08L 71/02

See application file for complete search history.

(56) References Cited

U.S. PATENT DOCUMENTS 3,177,223 A 4/1965 Erner
6,165,969 A 12/2000 Dieter
(Continued)

FOREIGN PATENT DOCUMENTS

CN 101812020 B 11/2011
JP 200255421 A 2/2002
(Continued)

OTHER PUBLICATIONS

Kiprianov et al., 29 Zhurnal Obschei Khimii 1290-9 (1959) (CAS Abstract) (Year: 1959).*

(Continued)

*Primary Examiner* — Timothy R Rozof
(74) *Attorney, Agent, or Firm* — HESLIN ROTHENBERG FARLEY & MESITI P.C.

(57) ABSTRACT

The invention provides: imidazole and imidazolium compounds of formulas (I) and (II):

(I)

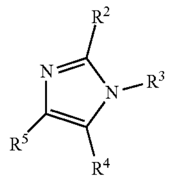

(II)

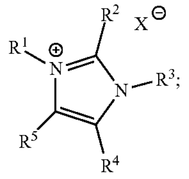

polymers containing a plurality of imidazolium-containing repeating units of formula (III'):

(III')

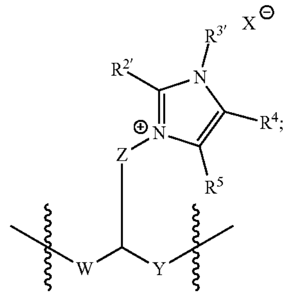

(Continued)

and membranes and devices comprising the polymers. Also provided are methods of making the inventive compounds and polymers.

16 Claims, No Drawings

Related U.S. Application Data

(60) Provisional application No. 62/147,388, filed on Apr. 14, 2015.

(51) Int. Cl.

| | |
|---|---|
| ***B01D 71/62*** | (2006.01) |
| ***C07D 233/58*** | (2006.01) |
| ***C07D 233/60*** | (2006.01) |
| ***C08F 8/30*** | (2006.01) |
| ***C08F 12/26*** | (2006.01) |
| ***C08F 210/14*** | (2006.01) |
| ***C08G 61/02*** | (2006.01) |
| ***C08G 61/06*** | (2006.01) |
| ***C08G 61/08*** | (2006.01) |
| ***C08L 25/18*** | (2006.01) |
| ***C08L 71/02*** | (2006.01) |
| ***H01M 8/1023*** | (2016.01) |
| ***H01M 50/414*** | (2021.01) |
| *C08F 26/06* | (2006.01) |
| *C08F 126/06* | (2006.01) |
| *C08F 212/14* | (2006.01) |
| *C08F 212/36* | (2006.01) |
| *C08F 226/06* | (2006.01) |
| *C08J 5/22* | (2006.01) |

(52) U.S. Cl.

CPC .................. *C08G 2261/149* (2013.01); *C08G 2261/3322* (2013.01); *C08G 2261/418* (2013.01); *C08G 2261/516* (2013.01); *C08G 2261/724* (2013.01); *C08J 5/2231* (2013.01); *C08J 2323/18* (2013.01); *C08J 2323/36* (2013.01); *C08L 2203/20* (2013.01); *H01M 2300/0082* (2013.01)

(56) References Cited

U.S. PATENT DOCUMENTS

| | | | |
|---|---|---|---|
| 6,355,231 | B1 | 3/2002 | Dieing |
| 6,512,079 | B2 | 1/2003 | Okamoto et al. |
| 9,200,118 | B2 | 12/2015 | Kharul et al. |
| 11,242,432 | B2 | 2/2022 | Coates et al. |
| 2006/0008670 | A1 | 1/2006 | Lin et al. |
| 2011/0020731 | A1 | 1/2011 | Yoshimura et al. |
| 2012/0157579 | A1 | 6/2012 | Parent et al. |
| 2013/0137011 | A1 | 5/2013 | Coates et al. |
| 2013/0296499 | A1 | 11/2013 | Coates et al. |
| 2014/0130416 | A1 | 5/2014 | Bara |
| 2015/0073063 | A1 | 3/2015 | Wright et al. |
| 2019/0047963 | A1 | 2/2019 | Coates et al. |

FOREIGN PATENT DOCUMENTS

| | | | |
|---|---|---|---|
| JP | 2009087687 | A | 4/2009 |
| JP | 2009-256654 | A | 11/2009 |
| JP | 6824902 | B2 | 2/2021 |
| KR | 1020120037934 | A | 4/2012 |
| KR | 1020120115848 | B1 | 10/2012 |
| WO | 2012075574 | A1 | 6/2012 |
| WO | 2013/012017 | A1 | 1/2013 |
| WO | 2014011661 | A2 | 1/2014 |
| WO | 2014046283 | A1 | 3/2014 |
| WO | 2016168468 | A2 | 10/2016 |

OTHER PUBLICATIONS

Shi et al., 51(S1) J. Heterocyclic Chem. E71-E76 (2014) (CAS Abstract) (Year: 2014).*

International Search Report and Written Opinion of the International Searching Authority for PCT/US2016/027543 mailed on Oct. 7, 2016.

PubChem CID: 22916417, Dec. 5, 2007.

Dong, H., et al., "Improving the Alkaline Stability of Imidazolium Cations by Substitution", ChemPhysChem, vol. 15, No. 14, pp. 3006-3014 (2014) (Abstract only).

Price, S.C., et al., "Relationships between Structure and Alkaline Stability of Imidazolium Cations for Fuel Cell Membrane Applications", ACS Macro Letters, vol. 3, No. 2, pp. 160-165 (2014) (Abstract only).

Wang, J., et al., "Stabilizing the Imidazolium Cation in Hydroxide-Exchange Membranes for Fuel Cells", ChemSusChem, vol. 6, pp. 2079-2082 (2013).

Finger, L.H., et al., "Access to pure and highly volatile hydrochalcogenide ionic liquids", vol. 51, pp. 16169-16172 (2015).

Si, Z., et al., "Effects of Substituents and Substitution Positions on Alkaline Stability of Imidazolium Cations and Their Corresponding Anion-Exchange Membranes", ACS Applied Materials & Interfaces, vol. 6, No. 6, pp. 4346-4355 (2014) (Abstract only).

Qui, B., et al., "Akaline imidazolium- and quaternary ammonium-functionalized anion exchange membranes for alkaline fuel cell applications", vol. 22, pp. 1040-1045 (2012) (Abstract only).

Zhang et al., "New Polyethylene Based Anion Exchange Membranes (PE-AEMs) with High Ionic Conductivity," Macromolecules, ACS Publications, 2011, pp. 5937-5946.

Long et al., "Hydroxide Degradation Pathways for Imidazolium Cations: A DFT Study," Journal of Physical Chemistry, 2014, pp. 9880-9888.

Hugar et al., "Imidazolium Cations with Exceptional Alkaline Stability: A Systematic Study of Structure—Stability Relationships," Journal of The American Chemical Society, Published Jun. 11, 2015, pp. 8730-8737.

Wang et al., "Cyclic Phosphoric Acid Catalyzed One-Pot, Four-Component Synthesis of 1,2,4,5-tetrasubsituted Imidazoles," Chinese Chemical Letters 23 (2012) 13-16, pp. 13-16.

Engel et al., "Imidazole und 1-Imidazolamine aus α-Acylaminoketiminen and α-Acylaminohydrazonen," Liebigs Ann. Chem. 1978, pp. 1916-1927 (and English translation thereof).

Keivanloo et al., "Boehmite Nanoparticles, an Efficient Green Catalyst for the Multi-Component Synthesis of Highly Substituted Imidazoles," Applied Catalysis A: General, 2013, pp. 291-300.

Ye et al., "Relative Chemical Stability of Imidazolium-Based Alkaline Anion Exchange Polymerized Ionic Liquids," Macromolecules, ACS Publications, 2011, pp. 8494-8503.

Lin et al., "Alkaline Stable C2-Substituted Imidazolium-Based Anion-Exchange Membranes," Chemistry of Materials, ACS Publications, 2013, pp. 1858-1867.

Martinez et al., "Ring-Opening Metathesis Polymerization of 8-Membered Cyclic Olefins," Polymer Chemistry, 2014, vol. 5, pp. 3507-3532.

Tsung-Han et al., "Thermally Cross-Linked Anion Exchange Membranes from Solvent Processable Isoprene Containing Ionomers," Macromolecules, ACS Publications, 2015, pp. 655-662.

Bader et al., "Acid-Catalysed Formation of Imidazoles from 2H-Azirines or Vinylazides and Nitriles," Helvetica Chimica Acta, vol. 61, Fasc.1, 1978, Nr. 23, pp. 286-304.

Samanta, Srikanta et al., Ni(II)-salt Catalyzed Activation of Primary Amine-sp3Ca—H and cyclization with 1, 2-diketone to tetrasubstituted imidazoles, Chemical Communications, 2014, 50(19), pp. 2477-2480.

Acke, Davy R. J. et al., "Continuous Synthesis of Tri- and Tetrasubstituted Imidazoles via a Multicomponent Reacting under Microreactor Conditions," QSAR & Combinatorial Science, 2006, 25(5-6), pp. 474-483.

Gelens, E. et al., "Efficient Library Synthesis of Imidazoles Using a Multicomponent Reaction and Microwave Irradiation," Molecular Diversity, 2006, 10(1), pp. 17-22.

(56) References Cited

OTHER PUBLICATIONS

Peppel, Tim et al., "Synthesis, Properties, and Structures of Salts with the Reineckate Anion, $[CR^{III}(NCS)_4(NH_3)_2]$-, and Large Organic Cations," Zeitshrift fuer Anorganische und Allgemeine Chemie, 2011, 637(10), pp. 1314-1321.

PubChem CID 71069201, National Center for Biotechnology Information. PubChem Database, FGSGFQWUPZQJOF-UHFFFAOYSA-N, CID=71069201, https://pubchem.ncbi.nim.nih.gov/compund/71069201 (accessed on Apr. 16, 2019), create date Mar. 21, 2013. (Year: 2013).

Han, Huijing et al. "Ring-Opening Metathesis Polymerization of Functionalized Cyclooctene by a Ruthenium-Based Catalyst in Ionic Liquid" Journal of Polymer Science Part A:Polymer Chemsitry, vol. 45, No. 17, (2007) pp. 3986-3993.

Liu, Ye et al. "Anion Transport in a Chemically Stable, Sterically Bulky a—C Modified Imidazolium Functionalized Anion Exchange Membrane" The Journal of Physical Chemistry, vol. 118, No. 28, (2014), pp. 15136-15145.

Bo Qiu et al: "Alkaline imidazolium- and quaternary ammonium-functionalized anion exchange membranes for alkaline fuel cell applications", Journal of Materials Chemistry, vol. 22, No. 3, (2012).

Extended European Search Report for EP Application No. 16780749.4 mailed Oct. 30, 2018.

Extended European Search Report for EP Application No. 22186960.5 dated Nov. 25, 2022.

* cited by examiner

IMIDAZOLES AND IMIDAZOLIUM CATIONS WITH EXCEPTIONAL ALKALINE STABILITY

CROSS REFERENCE TO RELATED APPLICATIONS

This application is a divisional of U.S. application Ser. No. 15/566,595, filed on Oct. 13, 2017, which is a § 371 national phase entry of International Application Number PCT/US2016/027543, filed on Apr. 14, 2016, which claims priority to U.S. Provisional Application No. 62/147,388, filed on Apr. 14, 2015. The entire contents of each of the prior applications are hereby incorporated herein by reference.

GOVERNMENT RIGHTS STATEMENT

This invention was made with Government support under Grant Number DE-SC0001086 awarded by US Department of Energy. The United States Government has certain rights in the invention.

BACKGROUND

With growing demand for clean and efficient energy, fuel cells have emerged as attractive electrochemical conversion devices due to their high energy density and their ability to produce energy more cleanly and efficiently compared to conventional systems, such as internal combustion engines. Proton exchange membrane fuel cells (PEMFCs) find use in many commercial applications. However, widespread production of PEMFCs is limited by the cost and durability of the materials used to produce them, such as platinum electrodes and electrolyte membrane.

In view of drawbacks associated with widespread production of PEMFCs, increased focus has been placed on alkaline fuel cells (AFCs), which operate by transporting hydroxide ions through the electrolyte under basic conditions. At elevated pH, oxygen reduction is more facile and lower overpotentials are required, thereby enabling the use of non-noble metal catalysts in AFCs. Indeed, the earliest examples of commercial fuel cells used aqueous potassium hydroxide solutions as the electrolyte medium to facilitate anion conduction. Unfortunately, the performance of these early fuel cells was compromised by exposure to carbon dioxide, a common component of feedstock gases, which reacts with hydroxide to produce carbonate salts. To overcome this issue, alkaline anion exchange membranes (AAEMs) can be used in alkaline fuel cells. AAEMs, which are generally comprised of organic cations covalently linked to a polymer backbone, are employed to prevent the formation of mobile salts and retain the conductive organic cation/hydroxide species.

Tetraalkylammonium cations have been appended to various polymer architectures to prepare AAEMs, including perfluorinated membranes, aromatic polysulfones, poly (arylene ethers), poly(arylene ether ketones), polyphenylenes, polystyrenes, and various aliphatic backbones. However, current ammonium cations (for example, the ubiquitous benzyl trimethylammonium (BTMA) cation) degrade rapidly under fuel cell operating conditions, which limits their utility and makes the improvement of AAEM stability a critical priority. Therefore, a need exists for moieties that offer enhanced stability under fuel cell operating conditions.

While certain aspects of conventional technologies have been discussed to facilitate disclosure of the invention, Applicant in no way disclaims these technical aspects, and it is contemplated that the claimed invention may encompass one or more of the conventional technical aspects discussed herein.

In this specification, where a document, act or item of knowledge is referred to or discussed, this reference or discussion is not an admission that the document, act or item of knowledge or any combination thereof was, at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

Briefly, the present invention satisfies the need for moieties that offer enhanced stability under fuel cell operating conditions. The present invention may address one or more of the problems and deficiencies of the art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

Certain embodiments of the presently-disclosed imidazoles and imidazolium cations, polymers incorporating imidazolium cations, and articles comprising the same, and related methods have several features, no single one of which is solely responsible for their desirable attributes. Without limiting the scope of the inventive compounds, polymers, articles, and methods as defined by the description and claims that follow, their more prominent features will now be discussed briefly. After considering this discussion, and particularly after reading the section of this specification entitled “Detailed Description of the Invention,” one will understand how the features of the various embodiments disclosed herein provide a number of advantages over the current state of the art. These advantages may include, without limitation, providing imidazole and imidazolium cations (and polymers incorporating imidazolium cations) that are easy to make and/or, for the compounds, to incorporate into polymers, that are resistant to degradation via nucleophilic or basic attack by hydroxide or methoxide, and/or that maintain favorable conductivity and stability in fuel cell devices.

Imidazole compounds and/or imidazolium cations that are stable under basic conditions are extremely important for several applications, including, without limitation: organocatalysts, solar cell electrolytes, phase-transfer catalysis, as carbon material precursors, as semiconductors in OLEDs (organic light emitting diodes), as ionic liquids, and cocatalysts. In general, the inventive compounds and polymers will be useful wherever base-stable organic cations and their precursors are required or beneficial. Moreover, embodiments of the inventive imidazoles and imidazolium cations can be readily incorporated into polymer architectures using several polymerization techniques, including but not limited to ring opening-metathesis (ROMP), controlled radical polymerization, and polymerization of functionalized α-olefins. Imidazole compounds may also be attached to preformed polymers by reacting with electrophilic sites existing in the polymer. Polymers with base-stable cations appended to the backbone are in demand for applications such as fuel cell membrane electrolytes, electrolysis, gas separation, desalination, anion exchange resins, nuclear waste remediation, and as stimuli-responsive materials. The inventive polymers may be useful anywhere that polymers containing base-stable cations are currently employed.

In one aspect, the invention provides a compound of formula (I) or (II):

(I)

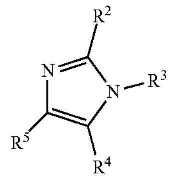

(II)

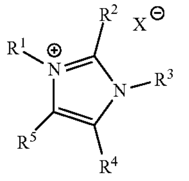

wherein:

$R^1$ is selected from $C_2$-$C_{16}$ hydrocarbyl, wherein one carbon atom of the $C_2$-$C_{16}$ hydrocarbyl may optionally be replaced by O;

$R^2$ is phenyl substituted with 0 to 3 substituents $R^6$ individually selected from $C_1$-$C_3$ alkyl;

$R^3$ is selected from $C_2$-$C_{16}$ hydrocarbyl;

$R^4$ and $R^5$ are individually selected from $C_1$-$C_{16}$ hydrocarbyl, or, taken together, $R^4$ and $R^5$, together with the carbon atoms to which they attached, form a ring selected from benzene, cyclooctene and norbornene; and $X^-$ is a counterion.

In a second aspect, the invention provides a polymer comprising a plurality of imidazolium-containing repeating units (IRUs) of formula (III'):

(III')

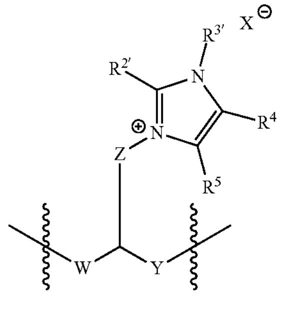

wherein:

$R^{2'}$ is selected from $C_1$-$C_6$ alkyl and $R^2$;

$R^2$ is phenyl substituted with 0 to 3 substituents $R^6$ individually selected from $C_1$-$C_3$ alkyl;

$R^{3'}$ is selected from hydrogen, methyl, and $R^3$;

$R^3$ is selected from $C_2$-$C_{16}$ hydrocarbyl;

$R^4$ and $R^5$ are individually selected from $C_1$-$C_{16}$ hydrocarbyl, or, taken together, $R^4$ and $R^5$, together with the carbon atoms to which they attached, form a ring selected from benzene, cyclooctene and norbornene;

$X^-$ is a counterion;

wavy lines indicate points of attachment to adjacent repeating units of the polymer;

W is a direct bond or $C_1$-$C_{10}$ hydrocarbyl;

Y is a direct bond or $C_1$-$C_{10}$ hydrocarbyl; and

Z is a direct bond or $C_1$-$C_{13}$ hydrocarbyl, wherein one carbon atom of the $C_1$-$C_{13}$ hydrocarbyl may optionally be replaced by O, provided that the sum of carbon atoms in W, Y, and Z is 1-15.

In a third aspect, the invention provides a membrane comprising a polymer according to the second aspect of the invention.

In a fourth aspect, the invention provides a device comprising a polymer according to the second aspect of the invention or a membrane according to the third aspect of the invention.

In a fifth aspect, the invention provides a method of determining the stability of a compound, said method comprising:

preparing a solution of the compound in basified methanol-$d_3$ ($KOH/CD_3OH$);

storing the solution; and analyzing the solution by $^1H$ NMR spectroscopy for amount of compound remaining relative to an internal standard.

These and other features and advantages of this invention will become apparent from the following detailed description of the various aspects of the invention taken in conjunction with the appended claims.

DETAILED DESCRIPTION OF THE INVENTION

Aspects of the present invention and certain features, advantages, and details thereof, are explained more fully below with reference to the non-limiting embodiments discussed herein. Descriptions of well-known materials, fabrication tools, processing techniques, etc., are omitted so as to not unnecessarily obscure the invention in detail. It should be understood, however, that the detailed description and the specific example(s), while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure.

The present invention provides imidazole and imidazolium compounds (including imidazolium monomers), and polymers comprising imidazolium functionalities (including residues of the inventive imidazolium compounds). It also provides methods of making the compounds and polymers. The compounds of the present invention find use as precursors to the inventive polymers, and as predictive indicators of stability of the inventive polymers, which can be used, for example, in membranes (e.g., fuel cell alkaline anion exchange membranes). The polymers are also useful in other applications, including electrolysis, gas separation, desalination and as stimuli-responsive materials.

Unless the context indicates otherwise, general definitions discussed with respect to formulas (I), (II), (III'), or (III) (e.g., for $R^1$ to $R^6$, X, W, Y, and Z) discussed herein include references to all other sub-formula sub-groups, preferences, embodiments and examples as defined herein (including the uses, methods and other aspects of the invention).

The prefixes "$C_x$-$C_y$" or "$C_{x-y}$" (where x and y are integers) as used herein refer to the number of carbon atoms in a given group. Thus, for example, a $C_1$-$C_6$alkyl (or $C_{1-6}$alkyl) group contains from 1 to 6 carbon atoms.

The term "hydrocarbyl" is a generic term encompassing aliphatic, alicyclic and aromatic groups having an all-carbon backbone, except where otherwise stated. Hydrocarbon refers to any substituent comprised of hydrogen and carbon as the only elemental constituents. In certain cases, as defined herein, one or more of the carbon atoms making up the carbon backbone may be replaced by a specified atom. Examples of hydrocarbyl groups include alkyl, cycloalkyl, cycloalkenyl, aryl, alkenyl, alkynyl, cycloalkylalkyl, cycloalkenylalkyl, and carbocyclic aralkyl, aralkenyl and aralkynyl groups (as well as alkylaralkyl, etc.). Such groups can be unsubstituted or, where stated, substituted by one or more substituents as defined herein. The examples and preferences expressed below apply to each of the hydrocarbyl substituent groups or hydrocarbyl-containing substituent groups referred to in the various definitions of substituents for compounds and polymers discussed herein unless the context indicates otherwise.

The number of carbon atoms in a given hydrocarbyl group are generally indicated using the prefix "$C_x$-$C_y$" ("$C_{x-y}$" may also be used). For example, discussed herein are $C_1$-$C_{16}$ hydrocarbyl groups (i.e., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ hydrocarbyl groups) and subgroups thereof (e.g., $C_2$-$C_{16}$ hydrocarbyl). Within the sub-set of hydrocarbyl, particular examples are $C_{1-10}$ hydrocarbyl groups, $C_{2-10}$ hydrocarbyl groups, $C_{1-7}$ hydrocarbyl groups (such as $C_{1-4}$ hydrocarbyl groups (e.g. $C_{1-3}$ hydrocarbyl groups or $C_{1-2}$ hydrocarbyl groups)), and $C_{2-7}$ hydrocarbyl groups (such as $C_{2-6}$ hydrocarbyl groups (e.g. $C_{2-4}$ hydrocarbyl groups or $C_{2-3}$ hydrocarbyl groups)).

The term "alkyl" as used herein as a group or part of a group refers to a linear or branched saturated hydrocarbon group containing a designated number of carbon atoms. Examples of such groups include, without limitation, methyl, ethyl, n-propyl, isopropyl, n-butyl, isobutyl, sec-butyl, tert-butyl, n-pentyl, isopentyl, neopentyl or hexyl and the like.

An "alkenyl" group refers to a linear or branched unsaturated hydrocarbon group containing at least one carbon-carbon double bond.

An "alkynyl" group refers to a linear or branched unsaturated hydrocarbon group containing at least one carbon-carbon triple bond.

The term "aryl" as used herein refers to carbocyclyl aromatic groups including phenyl, naphthyl, indenyl, and tetrahydronaphthyl groups.

The term "cycloalkyl" as used herein refers to a saturated monocyclic hydrocarbon ring having a designated number of carbon atoms. Examples of such groups include cyclopropyl, cyclobutyl, cyclopentyl, cyclohexyl, cycloheptyl or cyclooctyl and the like.

The term "cycloalkenyl" as used herein refers to a monocyclic hydrocarbon ring having a carbon carbon double bond.

Examples of cycloalkylalkyl, cycloalkenylalkyl, carbocyclic aralkyl, aralkenyl and aralkynyl groups include phenethyl, benzyl, styryl, phenylethynyl, cyclohexylmethyl, cyclopentylmethyl, cyclobutylmethyl, cyclopropylmethyl and cyclopentenylmethyl groups.

In one aspect, the invention provides a compound of formula (I) or (II):

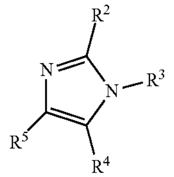
(I)

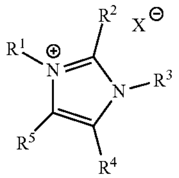
(II)

wherein:

$R^1$ is selected from $C_2$-$C_{16}$ hydrocarbyl, wherein one carbon atom of the $C_2$-$C_{16}$ hydrocarbyl may optionally be replaced by O;

$R^2$ is phenyl substituted with 0 to 3 substituents $R^6$ individually selected from $C_1$-$C_3$ alkyl;

$R^3$ is selected from $C_2$-$C_{16}$ hydrocarbyl;

$R^4$ and $R^5$ are individually selected from $C_1$-$C_{16}$ hydrocarbyl, or, taken together, $R^4$ and $R^5$, together with the carbon atoms to which they attached, form a ring selected from benzene, cyclooctene and norbornene; and $X^-$ is a counterion.

As shown above, compounds of formula (I) are imidazole compounds (wherein $R^1$ is not present), and compounds of formula (II) are positively charged imidazolium cations.

$R^1$ is selected from $C_2$-$C_{16}$ hydrocarbyl (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ hydrocarbyl), wherein one carbon atom (and hydrogen atoms attached to said carbon atom) of the $C_2$-$C_{16}$ hydrocarbyl may optionally be replaced by oxygen (O).

In some embodiments, $R^1$ is selected from $C_2$-$C_{16}$ hydrocarbyl (wherein no carbon atom is replaced by O).

In some embodiments, $R^1$ is selected from $C_2$-$C_{16}$ hydrocarbyl (or any subgroup thereof), wherein one carbon atom, which is not at the point of attachment of $R^1$ to the nitrogen at position 1 of the imidazole ring, is replaced by O.

In some embodiments, $R^1$ is selected from $C_2$-$C_{12}$ hydrocarbyl, wherein one carbon atom of the $C_2$-$C_{12}$ hydrocarbyl may optionally be replaced by O.

In some embodiments, $R^1$ is selected from $C_2$-$C_{10}$ hydrocarbyl, wherein one carbon atom of the $C_2$-$C_{10}$ hydrocarbyl may optionally be replaced by O.

In some embodiments, $R^1$ is selected from $C_2$-$C_7$ hydrocarbyl, wherein one carbon atom of the $C_2$-$C_7$ hydrocarbyl may optionally be replaced by O.

In some embodiments, $R^1$ is selected from $C_2$-$C_4$ hydrocarbyl, wherein one carbon atom of the $C_2$-$C_4$ hydrocarbyl may optionally be replaced by O.

In some embodiments, $R^1$ is selected from $C_2$-$C_8$ alkyl, wherein one carbon atom of the $C_2$-$C_8$ alkyl may optionally be replaced by O.

In some embodiments, $R^1$ is selected from $C_2$-$C_6$ alkyl, wherein one carbon atom of the $C_2$-$C_6$ alkyl may optionally be replaced by O.

In some embodiments, $R^1$ is selected from ethyl, n-propyl, isopropyl, n-butyl, isobutyl, sec-butyl, tert-butyl, n-pentyl, isopentyl, neopentyl, and hexyl, wherein one carbon atom may optionally be replaced by O.

In some embodiments, $R^1$ is an alkylaralkyl group, wherein one carbon atom of the alkylaralkyl group may optionally be replaced by O. For example, in some embodiments, $R^1$ is $H(CH_2)_p$—$(Ph)_q$-$(CH_2)_r$—*, wherein: * represents the point of attachment to the nitrogen at position 1 of the imidazole; p is 1-6; q is 0 or 1; and r is 1-6, provided that the total number of carbon atoms in $R^1$ is 2-16, and wherein one carbon atom may optionally be replaced by O. As used herein, the abbreviation "Ph" represents phenyl.

In some embodiments, $R^1$ is $H(CH_2)_p$—$(Ph)_q$-$(CH_2)_r$—*, wherein: * represents the point of attachment to the nitrogen at position 1 of the imidazole; p is 1-6; q is 0 or 1; and r is 1-6, provided that the total number of carbon atoms in $R^1$ is 2-16, and wherein one carbon atom of the $(CH_2)_p$ may optionally be replaced by O.

In some embodiments, $R^1$ is:

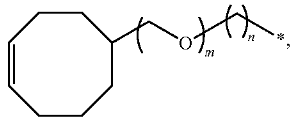

wherein:

* represents the point of attachment to the nitrogen atom at position 1 of the imidazolium ring;

m is 0 or 1; and n is 1-8, provided that the sum of m+n does not exceed 8. These embodiments (and other embodiments having other strained cyclo olefin rings in $R^1$) find particular use in Ring Opening Metathesis Polymerization (ROMP), which, as discussed below, is one technique that can be used to incorporate imidazolium cations in polymers.

In some embodiments, $R^1$ is benzyl.

In some embodiments, $R^1$ is not benzyl.

$R^2$ is phenyl substituted with 0 to 3 substituents $R^6$ (i.e., substituted with $R^6$ 0, 1, 2, or 3 times). Each $R^6$ (if present) is individually selected from $C_1$-$C_3$ alkyl.

The applicant has discovered that imidazolium cation compounds comprising a phenyl group at $R^2$ are more base-stable than those with alkyl groups. This observation contrasts with trends observed by Lin et al., *Chem. Mater.,* 25, 1858 (2013), where alkyl substituents improved stability compared to phenyl groups.

In some embodiments, $R^2$ is unsubstituted phenyl.

In some embodiments $R^2$ is substituted with $R^6$ 1-3 times, and each $R^6$ is individually selected from methyl, ethyl, n-propyl, and isopropyl.

In some embodiments $R^2$ is a moiety of formula ($R^{2a}$):

($R^{2a}$)

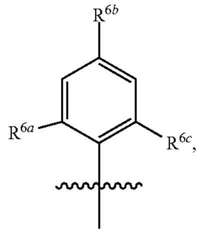

wherein:

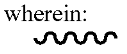 represents the point of attachment to the imidazole or imidazolium ring; and $R^{6a}$, $R^{6b}$, and $R^{6c}$ are individually selected from hydrogen and $C_1$-$C_3$ alkyl.

In some embodiments, at least two of $R^{6a}$, $R^{6b}$, and $R^{6c}$ are individually selected from methyl and isopropyl.

$R^3$ is selected from $C_2$-$C_{16}$ hydrocarbyl (i.e., $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$ hydrocarbyl).

In some embodiments, $R^3$ is selected from $C_2$-$C_{12}$ hydrocarbyl.

In some embodiments, $R^3$ is selected from $C_2$-$C_{10}$ hydrocarbyl.

In some embodiments, $R^3$ is selected from $C_2$-$C_7$ hydrocarbyl.

In some embodiments, $R^3$ is selected from $C_2$-$C_4$ hydrocarbyl.

In some embodiments, $R^3$ is selected from $C_2$-$C_8$ alkyl.

In some embodiments, $R^3$ is selected from $C_2$-$C_6$ alkyl.

In some embodiments, $R^3$ is selected from ethyl, n-propyl, isopropyl, n-butyl, isobutyl, sec-butyl, tert-butyl, n-pentyl, isopentyl, neopentyl, and hexyl.

In some embodiments, $R^3$ is benzyl.

In some embodiments, $R^3$ is not benzyl.

$R^4$ and $R^5$ are individually selected from $C_1$-$C_{16}$ hydrocarbyl, or, taken together, $R^4$ and $R^5$, together with the carbon atoms to which they attached, form a ring selected from benzene, cyclooctene and norbornene.

In some embodiments, $R^4$ and $R^5$ are individually selected from $C_1$-$C_{12}$ hydrocarbyl.

In some embodiments, $R^4$ and $R^5$ are individually selected from $C_1$-$C_{10}$ hydrocarbyl.

In some embodiments, $R^4$ and $R^5$ are individually selected from $C_1$-$C_7$ hydrocarbyl.

In some embodiments, $R^4$ and $R^5$ are individually selected from $C_1$-$C_4$ hydrocarbyl.

In some embodiments, $R^4$ and $R^5$ are individually selected from $C_1$-$C_8$ alkyl.

In some embodiments, $R^4$ and $R^5$ are individually selected from $C_1$-$C_6$ alkyl.

In some embodiments, $R^4$ and $R^5$ are individually selected from methyl, ethyl, n-propyl, isopropyl, n-butyl, isobutyl, sec-butyl, tert-butyl, n-pentyl, isopentyl, neopentyl, and hexyl.

In some embodiments, $R^4$ and $R^5$ are individually selected from $C_1$-$C_6$ alkyl and phenyl optionally substituted with $C_1$-$C_3$ alkyl.

$X^-$ is a counterion.

In some embodiments, $X^-$ is selected from hydroxide, halide, bicarbonate, carbonate, nitrate, cyanide, carboxylate and alkoxide.

In particular embodiments, $X^-$ is hydroxide.

In some embodiments, $X^-$ is halide selected from fluoride ($F^-$), chloride ($Cl^-$), bromide ($Br^-$), and iodide ($I^-$).

In some embodiments, the total number of carbon atoms in $R^1$-$R^6$ is 10-greater than or equal to 10.

In some embodiments, the total number of carbon atoms in $R^1$-$R^6$ is 10-60, (i.e., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 carbon atoms) including any and all ranges and subranges therein (e.g., 10-50, 15-45, 18-45, etc.).

In some embodiments, the invention provides a compound of formula (I), wherein $R^3$ is selected from $C_2$-$C_{12}$ hydrocarbyl, or of formula (II), wherein $R^1$ and $R^3$ are independently selected from $C_2$-$C_{12}$ hydrocarbyl.

In some embodiments, the invention provides a compound of formula (I), wherein $R^3$ is selected from $C_2$-$C_7$ hydrocarbyl, or of formula (II), wherein $R^1$ and $R^3$ are independently selected from $C_2$-$C_7$ hydrocarbyl.

In some embodiments, the invention provides a compound of formula (I), wherein $R^3$ is selected from $C_2$-$C_4$ alkyl and benzyl, or of formula (II), wherein $R^1$ and $R^3$ are independently selected from $C_2$-$C_4$ alkyl and benzyl.

In some embodiments, the invention provides a compound wherein $R^4$ and $R^5$ are individually selected from phenyl and $C_1$-$C_3$ alkyl.

In some embodiments, the invention provides a compound wherein $R^2$ is the moiety $R^{2a}$ shown above, and the compound is:

of formula (I), wherein: $R^3$ is n-butyl; $R^{6a}$ and $R^{6c}$ are methyl, and $R^{6b}$ is hydrogen; and $R^4$ and $R^5$ are individually selected from phenyl and methyl; or of formula (II), wherein: $R^1$ and $R^3$ are each n-butyl; $R^{6a}$ and $R^{6c}$ are methyl, and $R^{6b}$ is hydrogen; and $R^4$ and $R^5$ are individually selected from phenyl and methyl.

In some embodiments, the invention provides a compound of formula (II), said compound being a monomer, e.g., of the formula (IIA), (IIB), or (IIC):

(IIA)

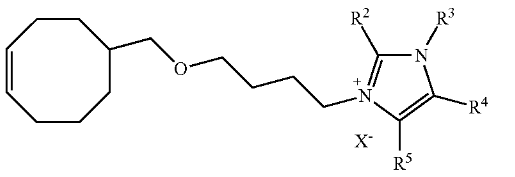

(IIB)

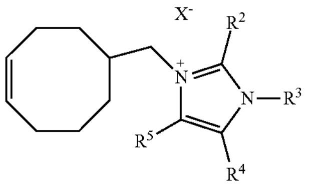

(IIC)

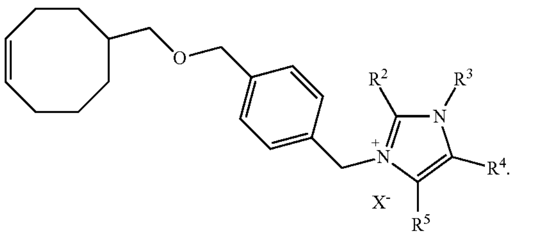

In some embodiments, the invention provides compounds having improved alkaline stability. As discussed above, imidazole compounds and/or imidazolium cations (and polymers containing such compounds) that are stable under basic conditions are extremely important for various applications.

In some embodiments, the invention provides a compound having an alkaline stability of between 75% and 100% cation remaining after 30 days in 5M KOH/$CD_3OH$ at 80° C., including any and all ranges and subranges therein (e.g., between 80% and 100%, between 85% and 100%, between 90% and 100%, between 95% and 100%, etc.). Said stability is determined by preparing solutions of the cation in basified methanol-$d_3$ (KOH/$CD_3OH$) and stored in flame-sealed NMR tubes at 80° C. At uniform time intervals, the solutions are analyzed by $1^H$ NMR spectroscopy for amount of cation remaining relative to an internal standard. The use of $CD_3OH$ precludes a hydrogen/deuterium exchange process that causes a reduction in the cation signals (not related to degradation) and obscures new product signals. Key aspects of cation degradation routes were revealed with this new protocol, which facilitates the design of new imidazoliums with strategically placed substituents to prevent decomposition.

In some embodiments, the invention provides a compound having an alkaline stability of greater than or equal to 80% cation remaining after 30 days in 5M KOH/$CD_3OH$ at 80° C. (e.g., greater than or equal to 80, 81, 82, 83, 84, 85, 86, 87, 88, 89, 90, 91, 92, 93, 94, 95, 96, 97, 98, or 99%).

In some embodiments, the invention provides a compound of formula (I):

(I)

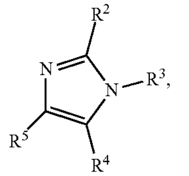

with $R^2$-$R^6$ and $X^-$ being defined as discussed above.

As discussed below, compounds of formula (I) are useful as intermediates in the preparation of polymers according to a second aspect of the invention (discussed below).

In some embodiments, the invention provides a compound of formula (II):

(II)

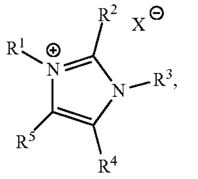

with $R^1$-$R^6$ and $X^-$ being defined as discussed above.

In addition to being useful when residues thereof are incorporated into polymers according to a second aspect of the invention (discussed below), compounds of formula (II) are also useful as predictive tools for assessing the stability of polymers according to the second aspect of the invention, and for various other applications, such as organocatalysts, solar cell electrolytes, phase transfer catalysts, and as carbon material precursors.

Imidazole compounds of formula (I) are a class of organic compounds that are readily amenable to synthesis because they can be prepared by a modular route, with easily modified substituents, and they are readily converted to imidazolium cations (e.g., of formula (II) via alkylation.

Methods of synthesizing imidazole and imidazolium compounds are well known in the art. In some embodiments, compounds of formula (I) or formula (II) are synthesized as shown below in Scheme 1:

SCHEME 1

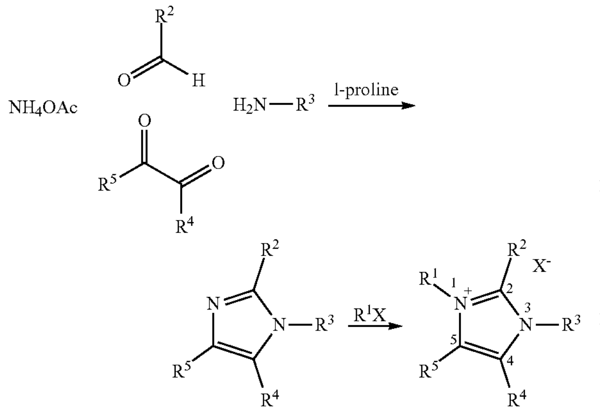

In a second aspect, the invention provides a polymer comprising a plurality of imidazolium-containing repeating units (IRUs) of formula (III'):

(III')

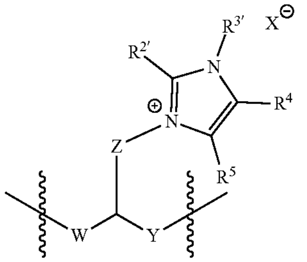

wherein:

$R^{2'}$ is selected from $C_1$-$C_6$ alkyl and $R^2$;

$R^2$ is phenyl substituted with 0 to 3 substituents $R^6$ individually selected from $C_1$-$C_3$ alkyl;

$R^{3'}$ is selected from hydrogen, methyl, and $R^3$;

$R^3$ is selected from $C_2$-$C_{16}$ hydrocarbyl;

$R^4$ and $R^5$ are individually selected from $C_1$-$C_{16}$ hydrocarbyl, or, taken together, $R^4$ and $R^5$, together with the carbon atoms to which they attached, form a ring selected from benzene, cyclooctene and norbornene;

$X^-$ is a counterion;

wavy lines indicate points of attachment to adjacent repeating units of the polymer;

W is a direct bond or $C_1$-$C_{10}$ hydrocarbyl;

Y is a direct bond or $C_1$-$C_{10}$ hydrocarbyl; and

Z is a direct bond or $C_1$-$C_{13}$ hydrocarbyl, wherein one carbon atom of the $C_1$-$C_{13}$ hydrocarbyl may optionally be replaced by O, provided that the sum of carbon atoms in W, Y, and Z is 1-15.

The polymers described herein contain imidazolium moieties. The polymers are desirable for use as, inter alia, alkaline anion exchange membranes (AAEMs) because their imidazolium cations provide enhanced stability under fuel cell operating conditions, as compared to other (e.g., ammonium) cations, which degrade rapidly under fuel cell operating conditions, limiting their utility and making the improvement of AAEM stability a critical priority. The fuel cells are constructed by methods well known in the art in which the membrane described herein can replace the anion exchange membrane of the art.

For polymers according to the second aspect of the invention, $R^2$-$R^6$ are as defined above with respect to the various embodiments of the first aspect of the invention.

W is a direct bond or $C_1$-$C_{10}$ hydrocarbyl.

In some embodiments, W is a direct bond or ($C_1$-$C_{10}$) alkylene (i.e., $C_1$, $C_2$, $C_3$, $C_4$, $C_5$, $C_6$, $C_7$, $C_8$, $C_9$, or $C_{10}$ alkylene). As would be understood by a person having ordinary skill in the art, alkylene refers to a bivalent alkyl group; an example would be $-CH_2CH_2CH_2CH_2CH_2CH_2CH_2CH_2-$.

Y is a direct bond or $C_1$-$C_{10}$ hydrocarbyl.

In some embodiments, Y is a direct bond or ($C_1$-$C_{10}$) alkylene (i.e., $C_1$, $C_2$, $C_3$, $C_4$, $C_5$, $C_6$, $C_7$, $C_8$, $C_9$, or $C_{10}$ alkylene).

In some embodiments, W is $(CH_2)_{1-5}$ and Y is $(CH_2)_{1-5}$.

Z is a direct bond or $C_1$-$C_{13}$ hydrocarbyl, wherein one carbon atom of the $C_1$-$C_{13}$ hydrocarbyl may optionally be replaced by O.

In some embodiments, Z comprises a phenylene moiety. Phenylene refers to a bivalent phenyl.

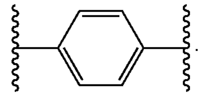 [SMILES: *c1ccc(*)cc1]

In some embodiments, the inventive polymers comprise a compound according to formula (I) or (II), or a residue thereof.

In some embodiments, the inventive polymer of formula (III') is a polymer according to formula (III):

(III)

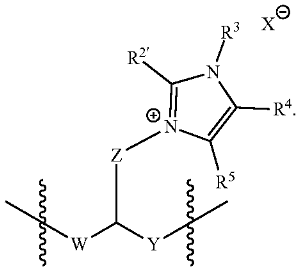

In some embodiments, the inventive polymer comprises a plurality of imidazolium-containing repeating units of formula (IIIA'):

(IIIA')

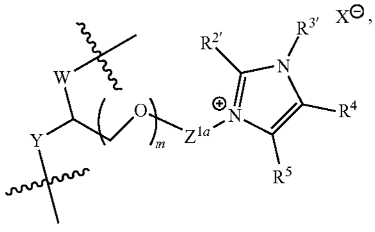

wherein:

m is 0 or 1; and $Z^{1a}$ is $C_1$-$C_{13}$ hydrocarbyl.

In some embodiments, the inventive polymer comprises imidazolium-containing repeating units of formula (IIIA):

(IIIA)

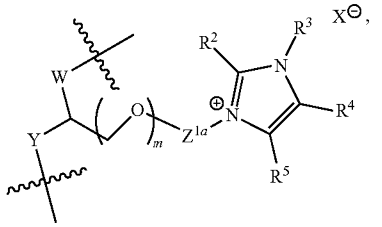

wherein:

m is 0 or 1; and $Z^{1a}$ is $C_1$-$C_{13}$ hydrocarbyl.

In some embodiments of polymers comprising imidazolium-containing repeating units of formula (IIIA') or (IIIA), m is 0.

In some embodiments of polymers comprising imidazolium-containing repeating units of formula (IIIA') or (IIIA), m is 1.

In some embodiments of polymers comprising imidazolium-containing repeating units of formula (IIIA') or (IIIA), $Z^{1a}$ is $C_1$-$C_{10}$ hydrocarbyl.

In some embodiments of polymers comprising imidazolium-containing repeating units of formula (IIIA') or (IIIA), $Z^{1a}$ is $C_1$-$C_8$ hydrocarbyl.

In some embodiments of polymers comprising imidazolium-containing repeating units of formula (IIIA') or (IIIA), $Z^{1a}$ is $-(CH_2)_p(Ph)_q-(CH_2)_r-$, wherein: p is 1-6; q is 0 or 1; and r is 1-6. In some embodiments, p is 1-2; q is 0 or 1; and r is 1-2.

In some embodiments, the inventive polymer comprises imidazolium-containing repeating units of formula (IIIB'):

(IIIB')

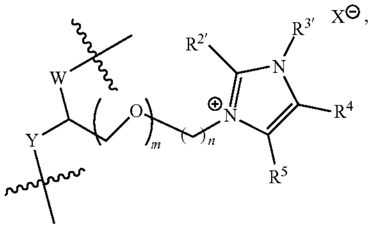

wherein:

m is 0 or 1; and n is 1-8.

In some embodiments, the inventive polymer comprises imidazolium-containing repeating units of formula (IIIB):

(IIIB)

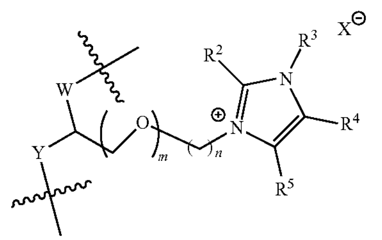

wherein:

m is 0 or 1; and n is 1-8.

In some embodiments, the polymer comprises a polyolefin or polystyrene backbone.

In some embodiments, the inventive polymer comprises imidazolium-containing repeating units of formula (IIIC') or (IIIC):

(IIIC')

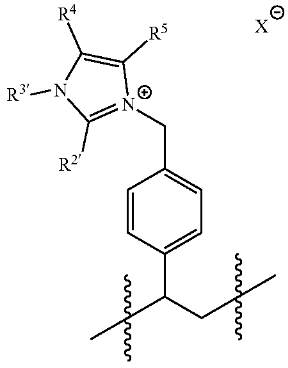

(IIIC)

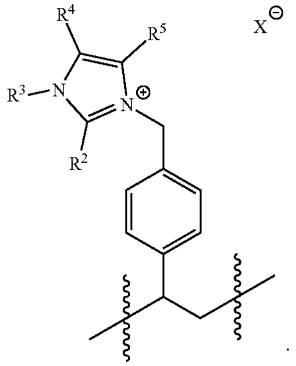

In some such embodiments, $X^-$ is halide.

In some embodiments of the inventive polymer, the sum of carbon atoms in W and Y is 1 or 3.

The polymers described herein can be cast or otherwise formed into membranes as described below. The membranes are useful in, e.g., hydrogen generation devices, fuel cells, and water purification devices.

In some embodiments, the polymer comprises, in addition to the IRUs, hydrocarbon repeating units (HRUs) and the polymers have the following structure:

$$*-[IRU]_{n'}-[HRU]_{1-n'}-*$$

wherein n' is from 0.05 to 1.0 and represents the mole fraction of IRU in the polymer. The IRU and HRU units may be random or sequentially placed. In some embodiments, n' is 0.1 to 0.4.

The polymers may be random or block copolymers. Adjacent IRU and HRU or IRU and IRU or HRU and HRU may be connected by a carbon-carbon single bond or a carbon-carbon double bond as illustrated below. In some embodiments, for example, when the polymer is to be used in an AAEM, at least some of the double bonds are reduced. In some embodiments, 50-100% (e.g., 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%) of the carbon-carbon double bonds are reduced to carbon-carbon single bonds.

The polymer can be crosslinked or not crosslinked. In some embodiments, the polymer is not cross-linked. An example of an embodiment of an unsaturated non-cross-linked polymer is shown in Structure I.

Structure I

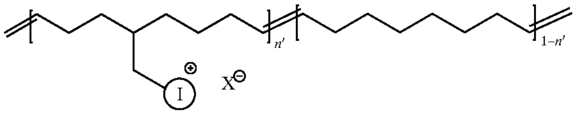

in which

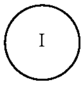

is an imidazolium residue.

An example of an embodiment of a saturated non-cross-linked polymer is shown in Structure II.

Structure II

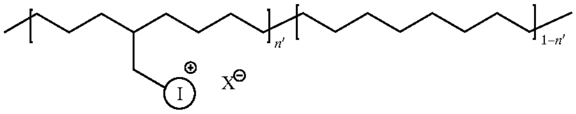

Embodiment of the inventive polymers can be synthesized by, for example, ring-opening metathesis polymerization (ROMP), which can be carried out using a transition metal (e.g., ruthenium-based) metathesis catalyst (e.g., a second generation Grubbs-type catalyst). The steps of the ROMP polymerization are known in the art. For example, the method includes the steps of providing a strained-ring monomer (or plurality of strained ring monomers) and a catalyst, such as a ruthenium-based alkene metathesis catalyst. The monomer(s) and catalyst are combined optionally in the presence of a solvent. The reaction mixture is heated under conditions such that a polymer is formed. By strained ring structure it is meant that at least one bond angle in the molecule differs from the optimal tetrahedral (109.5°) (for $sp^3$ bonds) or trigonal planar (120°) (for $sp^2$ bonds) bond angles such that the ground state energy of the carbocycle is above that of a carbocycle having all normal bond angles.

For ROMP, an imidazolium monomer (IM) (some embodiments of which are encompassed by the formula (II) genus) from which an IRU is derived is a hydrocarbon which has at least one alkene group that can be polymerized. The IM can have multiple alkene moieties which can result in the polymer being crosslinked as a result of polymerization of two alkene moieties from two different IM units. For example, an IM and a monomer with multiple alkene functional groups can be copolymerized to provide cross-linked polymers.

In a third aspect, the invention provides a membrane comprising a polymer according to the second aspect of the invention.

In a fourth aspect, the invention provides a device comprising a polymer according to the second aspect of the invention or a membrane according to the third aspect of the invention.

In some embodiments, the device is selected from a fuel cell, hydrogen generator, water purification device, and the like. In some embodiments, the device is a fuel cell. The fuel cell may additionally comprise an anode, a cathode, and a catalyst. In particular embodiments, the invention provides a fuel cell operating under alkaline conditions comprising an alkaline anion exchange membrane (AAEM) comprising a polymer of formula (III') or (III).

Within a fuel cell, the ion exchange membrane serves as the conducting interface between the anode and cathode by transporting the ions while being impermeable to gaseous and liquid fuels. It is desirable that an ion exchange membrane have the four properties listed below:

(1) low methanol solubility—complete insolubility being the ideal;

(2) hydroxide conductivity of from 1 mS/cm to 300 mS/cm—hydroxide conductivities of at 1, 5, 10, 25, 50, 100, 150, 200 and 300 mS/cm being increasingly desirable;

(3) mechanical properties such that a membrane comprising an ionomer does not tear or fracture under fuel cell operating conditions; and (4) as little swelling and hydrogel formation under alkaline fuel cell conditions as possible. Swelling less than 20% of original AAEM film thickness is ideal.

In some embodiments of the third aspect of the invention (directed to a membrane comprising a polymer according to the second aspect of the invention), the membrane is an AAEM comprising the inventive polymer. Embodiments of the AAEM display the desirable properties set forth above. In some embodiments, the thickness of the AAEM comprising the polymer materials described herein is from 1 to 300 μm (e.g., 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 μm), including any and all ranges and subranges therein.

In a fifth aspect, the invention provides a method of determining the stability of a compound (e.g., an imidazolium cation), said method comprising: preparing a solution of the compound in basified methanol-$d_3$ ($KOH/CD_3OH$); storing the solution (e.g., in sealed NMR tubes at a 80° C.); and analyzing the solution by $^1H$ NMR spectroscopy for amount of compound remaining relative to an internal standard. The use of $CD_3OH$ precludes a hydrogen/deuterium exchange process that causes a reduction in the compound signals (not related to degradation) and obscures new product signals. Embodiments of the method are also useful in revealing aspects of compound (e.g., imidazolium cation) degradation routes, and in designing new compounds.

EXAMPLES

The following examples are presented to illustrate the present invention. They are not intended to be limiting in any manner.

Methods and Instruments

Flash chromatography was performed with silica gel (particle size 40-64 mm, 230-400 mesh) using either mixtures of ethyl acetate and hexanes, diethylether and hexanes or mixtures of dichloromethane and methanol as the eluent. $^1H$ and $^{13}C$ NMR spectra were recorded on a Varian INOVA 500 or 600 MHz instrument at 22° C. with shifts reported relative to the residual solvent peak ($CD_3OD$ or $CD_3OH$); 3.31 ppm ($^1H$) and 49.00 ppm ($^{13}C$) or $CDCl_3$; 7.26 ppm ($^1$H) and 77.16 ppm ($^{13}$C)). High resolution mass spectrometry (DART-HRMS) analyses were performed on a Thermo Scientific Exactive Orbitrap MS system equipped with an Ion Sense DART ion source.

Solvent Suppression Procedure

Quantitative $^1$H NMR spectra for model compound stability studies were acquired in $CD_3OH$ to 1) prevent unwanted hydrogen/deuterium exchange in model compounds and degradation products and 2) improve the solubility of model compounds and degradation products. The —OH signal in $CD_3OH$ was suppressed by presaturation with a 2 second presaturation delay and continuous wave irradiation with decoupler field strength (γB1) of 113 Hz (equivalent to a presaturation power of 9). Spectra were acquired over a spectral width of −1 to 14 ppm with 60 second relaxation delay and nominal 90° excitation pulse. 16 scans were averaged for each analysis. NMR spectra were processed using MestReNova Version 9.0.1-13254 (Mestrelab Research S.L). Residual —OH signal was further suppressed with the signal suppression feature in the software. Spectra were zero-filled to 256k complex points and an exponential window function of 0.2 Hz was applied prior to manual phase correction. Whittaker smoother baseline correction was applied and linear correction was used for all integrals. Note: Residual signals between 5.5-7.0 ppm often derive from solvent suppression.

Chemicals

Benzaldehyde, 2,6-dimethylbenzaldehyde, 2-methylproprionaldehyde, ethanal, 2,3-butandione, diphenylethanedione, n-butylamine, 2M methyl amine in methanol, 2M ethyl amine in methanol, L-proline, benzyl bromide, ethyl iodide, n-butyl iodide, 2-iodopropane, 1-methyl imidazole and 1,2-dimethyl imidazole were purchased from Aldrich and used as received. Benzyl amine and methyl iodide were purchased form Alfa Aesar and used as received. Ammonium acetate, dichloromethane, ethyl acetate and chloroform were purchased from Fischer and used as received. Trimethyl amine (31-35% in ethanol) was purchased from Fluka and used and received. 3-(Trimethylsilyl)-1-propanesulfonic acid sodium salt and 1,2,4,5-tetramethylimidazole were purchased from TCI Chemicals and used as received. Methanol-d3 was purchased from Acros and used as received. Methanol-d4 and chloroform-d were purchased from Cambridge Isotope Laboratories. Methanol, hexanes and acetonitrile were purchased from Macron and used as received. Tetrahydrofuran magnesium sulfate and diethyl ether were purchased from J.T. Baker and used as received. Potassium hydroxide was purchased from Mallinckrodt and used as received.

Synthetic Procedures

General Procedure A: Multicomponent synthesis of substituted imidazoles: The appropriate aldehyde, dione and primary amine were combined with ammonium acetate and L-proline in methanol and stirred at 60° C. for 12 hours. After cooling to 22° C., the solvent was removed under reduced pressure. The residue was dissolved in chloroform, washed with $H_2O$, dried with magnesium sulfate, filtered and concentrated under reduced pressure. The crude product was further purified via recrystallization, flash column chromatography or a combination of both.

General Procedure B: Quaternization of imidazoles with alkyl or benzyl halides: The appropriate imidazole precursor was dissolved in acetonitrile and halide reagent was added while stirring. The mixture was stirred at 80° C. for 12 hours. After cooling to room temperature, the solvent was removed under reduced pressure. The residue was dissolved in chloroform and purified by precipitation into ether, ethyl acetate, methanol or tetrahydrofuran. Precipitation was repeated to obtain pristine products. Note: To obtain salts without residual solvent, the powders were mixed with a small portion of dichloromethane and solvent was removed under reduced pressure.

Synthesis of Imidazoles

1-Benzyl-2-(2,6-dimethylphenyl)-4,5-dimethyl-1H-imidazole (IM-3a)

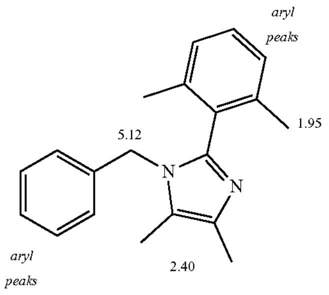 [SMILES: Cc1cccc(C)c1-c1nc(C)c(C)n1Cc1ccccc1]

Following general procedure A, 2,6-dimethylbenzaldehyde (1.00 g, 7.45 mmol), 2,3-butanedione (0.65 ml, 7.5 mmol), benzylamine (0.81 ml, 7.5 mmol) and ammonium acetate (0.574 g, 7.45 mmol) were combined with L-proline (0.136 g, 1.18 mmol) in methanol (30 ml). The residue was purified via flash column chromatography (2% methanol/dichloromethane) to give IM-3a (0.359 g, 17%) as an orange oil. $^1$H NMR (600 MHz, $CD_3OD$): δ 7.46 (t, J=7.7 Hz, 1H), 7.34-7.27 (m, 3H), 7.23 (d, J=7.7 Hz, 2H), 6.94 (dm, J=7.6 Hz, 2H), 5.12 (s, 2H), 2.40 (s, 3H), 2.40 (s, 3H), 1.95 (s, 6H). $^{13}$C NMR (126 MHz, $CD_3OD$): δ 143.80, 140.52, 134.95, 133.52, 130.12, 129.74, 129.42, 128.50, 128.47, 127.29, 123.78, 50.05, 19.67, 9.31, 9.01. HRMS (DART) m/z calculated for $C_{15}H_{21}N_2$+ (M+H+) 291.18558, found 291.18515.

1-Benzyl-4,5-dimethyl-2-phenyl-1H-imidazole (IM-3b)

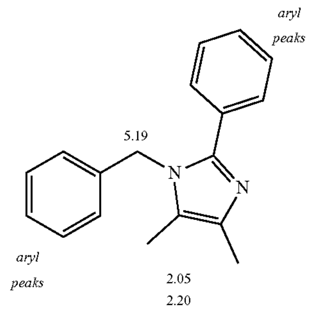 [SMILES: Cc1nc(-c2ccccc2)n(Cc2ccccc2)c1C]

Following general procedure A, benzaldehyde (5.0 ml, 49 mmol), 2,3-butanedione (4.3 ml, 49 mmol), benzylamine (5.9 ml, 54 mmol) and ammonium acetate (3.78 g, 49.0 mmol) were combined with L-proline (0.846 g, 7.35 mmol) in methanol (100 ml). The residue was purified via flash column chromatography (50% ethyl acetate/hexanes). The product was recrystallized from acetonitrile to give IM-3b (2.54 g, 20%) as an pale yellow powder. $^1$H NMR (500 MHz, $CD_3OD$): δ 7.45 (m, 2H), 7.38 (m, 3H), 7.32 (t, J=7.4 Hz, 2H), 7.30-7.24 (t, J=7.4 Hz, 1H), 6.98-6.94 (d, J=7.6 Hz, 2H), 5.19 (s, 2H), 2.20 (s, 3H), 2.05 (s, 3H). $^{13}$C NMR (126 MHz, $CD_3OD$): δ 147.56, 138.54, 133.91, 131.73, 130.00, 129.96, 129.69, 129.66, 128.57, 126.65, 125.57, 48.71, 12.38, 8.98. HRMS (DART) m z calculated for $C_{18}H_{19}N_2^+$ (M+H$^+$) 263.15428, found 263.15349.

1-Benzyl-2-isopropyl-4,5-dimethyl-1H-imidazole_ (IM-3c)

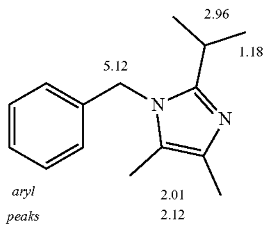

Following general procedure A, 2-methylproprionaldehyde (5.2 ml, 57 mmol), 2,3-butanedione (5.0 ml, 57 mmol), benzylamine (6.2 ml, 57 mmol) and ammonium acetate (4.40 g, 57.0 mmol) were combined with L-proline (0.984 g, 8.55 mmol) in methanol (100 ml). The residue was purified via flash column chromatography (1:10:90 triethylamine/methanol/dichloromethane). The product was recrystallized from acetonitrile at −20° C. and sublimed to give IM-3c (0.841 g, 6.5%) as a white powder. $^1$H NMR (600 MHz, $CD_3OD$): δ 7.31 (t, J=7.6 Hz, 2H), 7.25 (t, J=7.4 Hz, 1H), 6.93 (d, J=7.8 Hz, 2H), 5.12 (s, 2H), 2.96 (hept, J=6.9 Hz, 1H), 2.12 (s, 3H), 2.01 (s, 3H), 1.18 (d, J=6.9 Hz, 6H). $^{13}$C NMR (126 MHz, $CD_3OD$): δ 152.94, 138.84, 132.04, 129.88, 128.49, 126.74, 123.08, 47.22, 27.17, 22.27, 12.14, 8.67. HRMS (DART) m/z calculated for $C_{15}H_{21}N_2^+$ (M+H$^+$) 229.16993, found 229.1705.

1-Benzyl-2-(2,6-dimethylphenyl)-4,5-diphenyl-1H-imidazole (IM-4a)

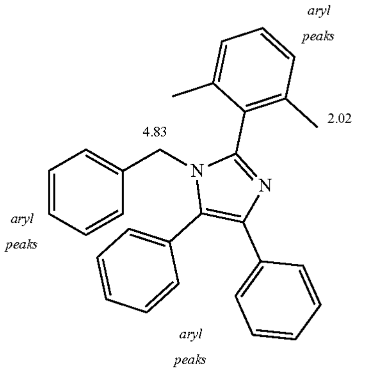 [SMILES: Cc1cccc(C)c1-c1nc(-c2ccccc2)c(-c2ccccc2)n1Cc1ccccc1]

Following general procedure A, 2,6-dimethylbenzaldehyde (1.00 g, 7.45 mmol), diphenylethanedione (1.57 g, 7.45 mmol), benzylamine (0.80 ml, 7.5 mmol) and ammonium acetate (0.574 g, 7.45 mmol) were combined with L-proline (0.129 g, 1.12 mmol) in methanol (30 ml). The residue was purified via flash column chromatography (10% ethyl acetate/hexanes). The product was recrystallized from acetonitrile to give IM-4a (0.787 g, 25%) as a white powder. $^1$H NMR (600 MHz, $CD_3OD$): δ 7.50-7.43 (m, 3H), 7.41 (m, 4H), 7.30 (t, J=7.6 Hz, 1H), 7.18 (tm, J=7.4 Hz, 2H), 7.16-7.10 (m, 4H), 7.06 (t, J=7.7 Hz, 2H), 6.59 (d, J=7.7 Hz, 2H), 4.83 (s, 2H), 2.02 (s, 6H). $^{13}$C NMR (126 MHz, $CDCl_3$): δ 146.54, 138.83, 137.41, 136.34, 134.78, 131.47, 131.31, 130.54, 129.27, 129.04, 128.57, 128.52, 128.12, 128.03, 127.49, 127.41, 127.38, 126.64, 126.15, 47.76, 19.93. HRMS (DART) m/z calculated for $C_{19}H_{31}N_2^+$ (M$^+$) 415.21688, found 415.21722.

2-(2,6-Dimethylphenyl)-1-methyl-4,5-diphenyl-1H-imidazole (IM2-4a)

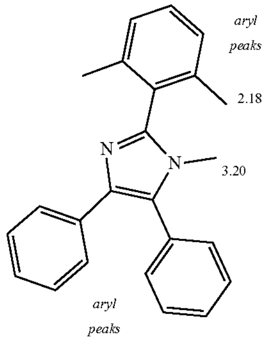 [SMILES: Cc1cccc(C)c1-c1nc(-c2ccccc2)c(-c2ccccc2)n1C]

Following general procedure A, 2,6-dimethylbenzaldehyde (2.08 g, 15.5 mmol), diphenylethanedione (3.26 mg, 15.5 mmol), 2M methylamine in methanol (7.8 ml, 16 mmol) and ammonium acetate (1.19 g, 15.5 mmol) were combined with L-proline (0.892 g, 7.75 mmol) in methanol (60 ml). The residue was purified via flash column chromatography (15% ethyl acetate/hexanes). The product was recrystallized from acetonitrile to give IM2-4a (1.30 g, 25%) as a white powder. $^1$H NMR (600 MHz, $CD_3OD$): δ 7.53-7.45 (m, 3H), 7.41 (m, 4H), 7.33 (t, J=7.6 Hz, 1H), 7.24-7.16 (m, 4H), 7.16-7.12 (t, J=7.3 Hz, 1H), 3.20 (s, 3H), 2.18 (s, 6H). $^{13}$C NMR (126 MHz, $CD_3OD$): δ 148.14, 140.11, 138.21, 135.51, 132.05, 132.04, 131.28, 130.98, 130.52, 130.21, 129.89, 129.13, 128.58, 128.19, 127.60, 31.73, 19.96. HRMS (DART) m/z calculated for $C_{24}H_{23}N_2^+$ (M+H$^+$) 339.18558, found 339.18505.

1-Methyl-2,4,5-triphenyl-1H-imidazole (IM-4b)

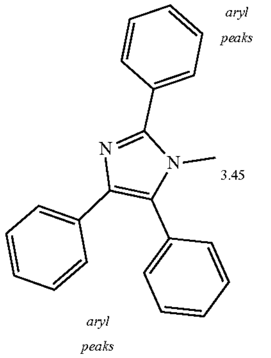 [SMILES: Cn1c(-c2ccccc2)nc(-c2ccccc2)c1-c1ccccc1]

Following general procedure A, benzaldehyde (2.5 ml, 25 mmol), diphenylethanedione (5.20 g, 24.7 mmol), 2M methylamine in methanol (12 ml, 25 mmol) and ammonium acetate (1.90 g, 24.7 mmol) were combined with L-proline (0.427 g, 3.70 mmol) in methanol (100 ml). The residue was recrystallized in methanol from give IM-4b (2.88 g, 38%) as a white powder. $^1$H NMR (600 MHz, $CD_3OD$): δ 7.69 (dm, J=7.7 Hz, 2H), 7.51 (m, 2H), 7.49-7.40 (m, 4H), 7.37 (m, 4H), 7.20-7.14 (m, 2H), 7.14-7.07 (tm, J=7.6 Hz, 1H), 3.45 (s, 3H). $^{13}$C NMR (126 MHz, $CDCl_3$): δ 147.93, 137.78, 134.72, 131.26, 131.01, 130.92, 130.52, 129.11, 129.09, 128.79, 128.62*, 128.13, 127.00, 126.35, 33.21. HRMS (DART) m/z calculated for $C_{22}H_{19}N_2^+$ (M+H$^+$) 311.15428, found 311.15334.

1-Benzyl-2,4,5-triphenyl-1H-imidazole (IM2-4b)

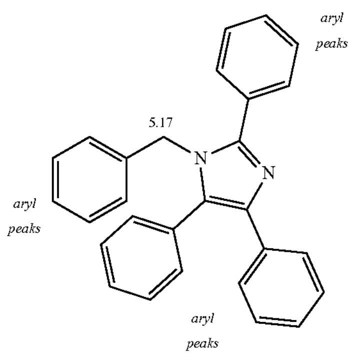 [SMILES: c1ccc(Cn2c(-c3ccccc3)nc(-c3ccccc3)c2-c2ccccc2)cc1]

Following general procedure A, benzaldehyde (2.0 ml, 20 mmol), diphenylethanedione (4.10 g, 19.6 mmol), benzylamine (2.1 ml, 20 mmol) and ammonium acetate (1.50 g, 19.6 mmol) were combined with L-proline (0.338 g, 2.94 mmol) in methanol (80 ml). The residue was purified via flash column chromatography (10% ethyl acetate/hexanes to 50% ethyl acetate/hexanes). The product was recrystallized in methanol at −20° C. from give IM2-4b (1.84 g, 24%) as a white powder. $^1$H NMR (600 MHz, $CD_3OD$): δ 7.66-7.61 (m, 2H), 7.48-7.45 (m, 3H), 7.45-7.41 (m, 2H), 7.41-7.31 (m, 3H), 7.26-7.23 (dm, J=7.8 Hz, 2H), 7.22-7.11 (m, 6H), 6.73 (dm, J=7.9 Hz, 2H), 5.17 (s, 2H). $^{13}$C NMR (126 MHz, $CDCl_3$): δ 148.11, 138.12, 137.58, 134.55, 131.10, 131.08, 131.02, 130.11, 129.09, 128.93, 128.83, 128.66, 128.63, 128.61, 128.13, 127.39, 126.82, 126.40, 126.04, 48.31. HRMS (DART) m z calculated for $C_{28}H_{23}N_2^+$ (M+H$^+$) 387.18558, found 387.18430.

1-Benzyl-2-isopropyl-4,5-diphenyl-1H-imidazole (IM-4c)

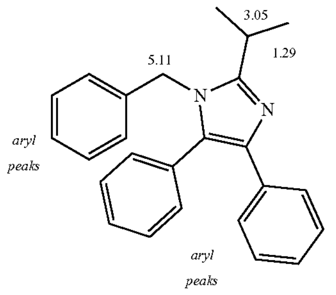 [SMILES: CC(C)c1nc(-c2ccccc2)c(-c2ccccc2)n1Cc1ccccc1]

Following general procedure A, 2-methylproprionaldehyde (2.5 ml, 28 mmol), diphenylethanedione (5.76 g, 27.4 mmol), benzylamine (3.0 ml, 27 mmol) and ammonium acetate (2.17 g, 27.4 mmol) were combined with L-proline (0.473 g, 4.11 mmol) in methanol (100 ml). The residue was purified via flash column chromatography (1:10:90 triethylamine/ethyl acetate/hexanes) to give IM-4c (2.41 g, 25%) as a white powder. $^1$H NMR (600 MHz, $CD_3OD$): δ 7.39-7.31 (m, 5H), 7.28 (t, J=7.4 Hz, 2H), 7.25-7.20 (m, 3H), 7.20-7.16 (tm, J=7.7 Hz, 2H), 7.16-7.11 (tm, J=7.4 Hz, 1H), 6.92 (d, J=7.6 Hz, 2H), 5.11 (s, 2H), 3.05 (hept, J=6.9 Hz, 1H), 1.29 (d, J=6.9 Hz, 6H). $^{13}$C NMR (126 MHz, $CD_3OD$): δ 155.14, 138.82, 138.21, 135.76, 132.27, 132.02, 129.90*, 129.80, 129.71, 128.99, 128.64, 128.55, 127.51, 126.89, 47.76, 27.69, 22.09. HRMS (DART) m/z calculated for $C_{25}H_{25}N_2^+$ (M+H$^+$) 353.20123, found 353.20105.

1-Benzyl-2-methyl-4,5-diphenyl-1H-imidazole (IM-4d)

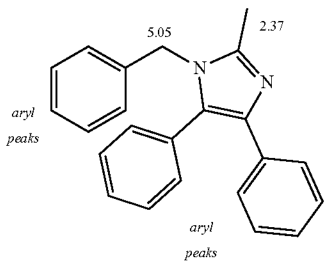 [SMILES: Cc1nc(-c2ccccc2)c(-c2ccccc2)n1Cc1ccccc1]

Following general procedure A, ethanal (2.0 ml, 36 mmol), diphenylethanedione (7.48 mg, 35.6 mmol), benzylamine (4.3 ml, 36 mmol) and ammonium acetate (2.74 g, 35.6 mmol) were combined with L-proline (0.615 g, 5.34 mmol) in methanol (30 ml). The residue was purified via flash column chromatography (1:20:80 triethylamine/ethyl acetate/hexanes). The product was recrystallized from acetonitrile at −20° C. to give IM-4d (0.652 g, 5.6%) as a white powder. $^1$H NMR (600 MHz, $CD_3OD$): δ 7.41-7.33 (m, 5H), 7.28 (tm, J=7.6 Hz, 2H), 7.25-7.19 (m, 3H), 7.17 (tm, J=7.4 Hz, 2H), 7.14-7.09 (tm, J=7.3 Hz, 1H), 6.92-6.89 (m, 2H), 5.05 (s, 2H), 2.37 (s, 3H). $^{13}$C NMR (126 MHz, $CD_3OD$): δ 146.63, 138.22, 137.45, 135.49, 132.19, 132.01, 130.61, 130.01, 129.89*, 129.09, 128.60, 128.06, 127.50, 127.00, 48.10, 13.16. HRMS (DART) m/z calculated for $C_{23}H_{21}N_2^+$ (M+H$^+$) 325.16993, found 325.1705.

2-(2,6-Dimethylphenyl)-1-ethyl-4,5-diphenyl-1H-imidazole (IM-5a)

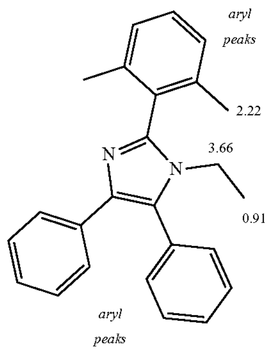 [SMILES: CCn1c(-c2c(C)cccc2C)nc(-c2ccccc2)c1-c1ccccc1]

Following general procedure A, 2,6-dimethylbenzaldehyde (1.00 g, 7.45 mmol), diphenylethanedione (1.57 g, 7.45 mmol), 2M ethylamine in methanol (7.5 ml, 15 mmol) and ammonium acetate (0.570 g, 7.45 mmol) were combined with L-proline (0.128 g, 1.12 mmol) in methanol (30 ml). The residue was purified via flash column chromatography (10% ethyl acetate/hexanes). The product was recrystallized from acetonitrile at −20° C. to give IM-5a (0.411 g, 16%) as a white powder. $^{1}$H NMR (600 MHz, $CD_3OD$): δ 7.52 (m, 3H), 7.44 (d, J=7.4 Hz, 2H), 7.38 (d, J=7.4 Hz, 2H), 7.34 (t, J=7.7 Hz, 1H), 7.22 (d, J=7.6 Hz, 2H), 7.18 (t, J=7.3 Hz, 2H), 7.15-7.11 (m, 1H), 3.66 (q, J=7.1 Hz, 2H), 2.22 (s, 6H), 0.91 (t, J=7.1 Hz, 3H). $^{13}$C NMR (126 MHz, $CD_3OD$): δ 147.37, 139.99, 138.57, 135.47, 132.33, 132.22, 131.45, 130.97, 130.30, 130.00, 129.86, 129.10, 128.73, 128.11, 127.54, 40.47, 20.19, 15.92. HRMS (DART) m/z calculated for $C_{25}H_{25}N_2^+$ (M+H$^+$) 353.20123, found 353.20028.

1-n-Butyl-2,4,5-triphenyl-1H-imidazole (IM-6b)

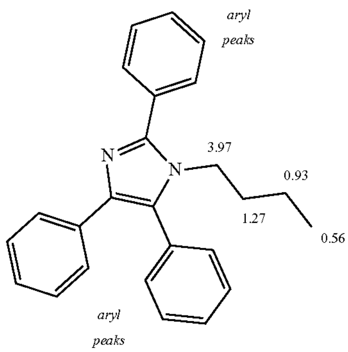 [SMILES: CCCCn1c(-c2ccccc2)nc(-c2ccccc2)c1-c1ccccc1]

Following general procedure A, benzaldehyde (2.0 ml, 20 mmol), diphenylethanedione (4.54 g, 21.6 mmol), n-butylamine (2.1 ml, 22 mmol) and ammonium acetate (1.51 g, 19.6 mmol) were combined with L-proline (0.260 g, 2.26 mmol) in methanol (80 ml). The residue was purified via flash column chromatography (10% ethyl acetate/hexanes to 100% ethyl acetate). The product was recrystallized from acetonitrile to give IM-6b (6.39 g, 93%) as a white powder. $^{1}$H NMR (600 MHz, $CD_3OD$): δ 7.71-7.66 (d, J=7.4 Hz, 2H), 7.58-7.45 (m, 6H), 7.44-7.36 (m, 4H), 7.21-7.16 (t, J=7.4 Hz, 2H), 7.16-7.11 (m, 1H), 4.00-3.93 (m, 2H), 1.27 (p, J=7.4 Hz, 2H), 0.93 (sext, J=7.4 Hz, 2H), 0.56 (t, J=7.4 Hz, 3H). $^{13}$C NMR (126 MHz, $CDCl_3$): δ 147.71, 137.73, 134.71, 131.66, 131.63, 131.08, 129.70, 129.24, 129.08, 128.82, 128.64*, 128.07, 126.85, 126.22, 44.55, 32.58, 19.49, 13.33. HRMS (DART) m/z calculated for $C_{25}H_{25}N_2^+$ (M+H$^+$) 353.20123, found 353.20124.

1-n-Butyl-2-(2,6-dimethylphenyl)-4,5-dimethyl-1H-imidazole (IM-7a)

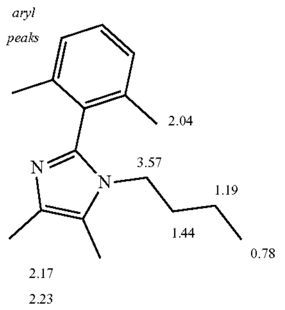 [SMILES: CCCCn1c(-c2c(C)cccc2C)nc(C)c1C]

Following general procedure A, 2,6-dimethylbenzaldehyde (2.00 g, 14.9 mmol), 2,3-butanedione (1.3 ml, 15 mmol), n-butylamine (1.5 ml, 15 mmol) and ammonium acetate (1.15 g, 14.9 mmol) were combined with L-proline (0.251 g, 2.24 mmol) in methanol (60 ml). The crude mixture was initially purified via flash column chromatography (5% methanol/dichloromethane to 50% methanol/dichloromethane) to afford a brown oil. The residue was further purified via flash column chromatography (5% ethyl acetate/hexanes to 100% ethyl acetate) to give IM-7a (0.554 g, 15%) as a pale brown oil. $^{1}$H NMR (600 MHz, $CD_3OD$): δ 7.27 (t, J=7.6 Hz, 1H), 7.14 (d, J=7.6 Hz, 2H), 3.63-3.48 (m, 2H), 2.23 (s, 3H), 2.17 (s, 3H), 2.04 (s, 6H), 1.49-1.40 (p, J=7.4 Hz, 2H), 1.19 (sext, J=7.4 Hz, 2H), 0.78 (t, J=7.4 Hz, 3H). $^{13}$C NMR (126 MHz, $CD_3OD$): δ 145.11, 139.87, 132.93, 131.97, 130.51, 128.50, 123.49, 44.78, 33.50, 20.78, 20.05, 13.79, 12.29, 8.95. HRMS (DART) m z calculated for $C_{17}H_{25}N_2^+$ (M+H$^+$) 257.201.23, found 257.20141.

1-n-Butyl-4,5-dimethyl-2-phenyl-1H-imidazole (IM-7b)

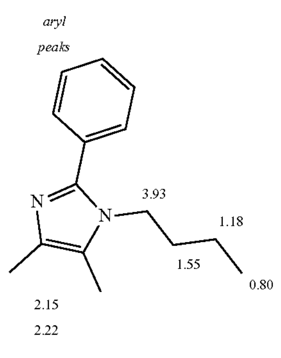 [SMILES: CCCCn1c(-c2ccccc2)nc(C)c1C]

Following general procedure A, benzaldehyde (2.0 ml, 20 mmol), 2,3-butanedione (1.9 ml, 22 mmol), n-butylamine (1.9 ml, 20 mmol) and ammonium acetate (1.51 g, 19.6 mmol) were combined with L-proline (0.260 g, 2.26 mmol) in methanol (80 ml). The residue was initially purified via flash column chromatography (50% ethyl acetate/hexanes) to give IM-7b (3.44 g, 77%) as a dark brown oil. Distillation under vacuum with a Hickman apparatus produced a pale yellow oil. $^1$H NMR (600 MHz, $CD_3OD$): δ 7.54-7.36 (m, 5H), 3.96-3.91 (m, 2H), 2.22 (s, 3H), 2.15 (s, 3H), 1.59-1.49 (p, J=7.4 Hz, 2H), 1.18 (sext, J=7.4 Hz, 2H), 0.80 (t, J=7.4 Hz, 3H). $^{13}$C NMR (126 MHz, $CD_3OD$): δ 147.03, 133.39, 132.53, 130.11, 129.88, 129.68, 124.91, 45.07, 33.76, 20.63, 13.78, 12.16, 8.97. HRMS (DART) m/z calculated for $C_{15}H_{21}N_2^+$ (M+H$^+$) 229.16993, found 229.16942.

1-n-Butyl-2-(2,6-dimethylphenyl)-4,5-diphenyl-1H-imidazole (IM-8a)

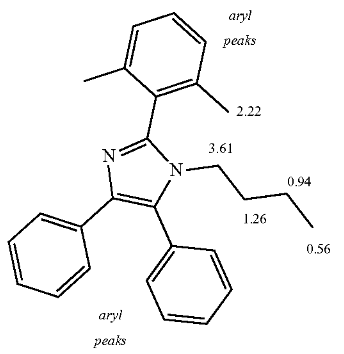 [SMILES: CCCCn1c(-c2c(C)cccc2C)nc(-c2ccccc2)c1-c1ccccc1]

Following general procedure A, 2,6-dimethylbenzaldehyde (2.00 g, 14.9 mmol), diphenylethanedione (3.13 g, 14.9 mmol), n-butylamine (1.5 ml, 15 mmol) and ammonium acetate (1.15 g, 14.9 mmol) were combined with L-proline (0.257 g, 2.26 mmol) in methanol (60 ml). The residue was purified via flash column chromatography (10% ethyl acetate/hexanes). The product was recrystallized in acetonitrile to give IM-8a (0.975 g, 17%) as a white powder. $^1$H NMR (600 MHz, $CD_3OD$): δ 7.55-7.46 (m, 3H), 7.44-7.41 (dm, J=7.4 Hz, 2H), 7.40-7.38 (dm, J=7.9 Hz, 2H), 7.34 (t, J=7.7 Hz, 1H), 7.22 (d, J=7.7 Hz, 2H), 7.19-7.15 (tm, J=7.6 Hz, 2H), 7.15-7.11 (tm, J=7.3 Hz, 1H), 3.63-3.59 (m, 2H), 2.22 (s, 6H), 1.26 (p, J=7.4 Hz, 2H), 0.94 (sext, J=7.4 Hz, 2H), 0.56 (t, J=7.4 Hz, 3H). $^{13}$C NMR (126 MHz, $CD_3OD$): δ 147.49, 139.87, 138.34, 135.44, 132.30, 132.21, 131.38, 130.90, 130.26, 130.06, 129.94, 129.10, 128.73, 128.08, 127.52, 45.10, 33.14, 20.48, 20.31, 13.52. HRMS (DART) m/z calculated for $C_{27}H_{29}N_2^+$ (M+H$^+$) 381.23253, found 381.23138.

Synthesis of Cations

Non-imidazolium cations (for comparative purposes) and imidazolium cations (both inventive and comparative) were prepared as follows.

Benzyl Trimethylammonium Bromide (1)

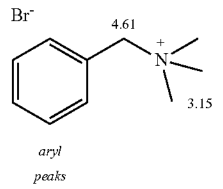

Trimethylamine, 30% in ethanol, (0.76 ml, 3.1 mmol) was treated with benzyl bromide (0.40 ml, 3.4 mmol) in acetonitrile (5 ml). The residue was dissolved in chloroform and purified via precipitation into ether to give 1 (0.693 g, 90%) as a white powder. $^1$H NMR (600 MHz, $CD_3OD$): δ 7.63-7.60 (dm, J=7.7 Hz, 2H), 7.59-7.52 (m, 3H), 4.61 (s, 2H), 3.15 (s, 9H). $^{13}$C NMR (126 MHz, $CD_3OD$): δ 134.10, 131.87, 130.26, 129.19, 70.15, 53.19, 53.16, 53.13. HRMS (DART) m/z calculated for $C_{10}H_{16}N^+$ (M$^+$) 150.12773, found 150.12750.

1-Benzyl-3-methylimidazolium bromide (2a)

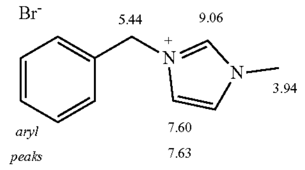

Following general procedure B, 1-methylimidazole (1.0 ml, 13 mmol) was treated with benzyl bromide (1.5 ml, 12 mmol) in acetonitrile (10 ml). The residue was dissolved in chloroform and purified via precipitation into ether to give 2a (3.03 g, 98%) as a brown oil. $^1$H NMR (600 MHz, $CD_3OD$): δ 9.06 (s, 1H), 7.64-7.62 (m, 1H), 7.61-7.58 (m, 1H), 7.47-7.40 (m, 4H), 5.44 (s, 2H), 3.94 (s, 3H). $^{13}$C NMR (151 MHz, $CD_3OD$): δ 137.97, 135.25, 130.39, 130.33, 129.71, 125.26, 123.66, 54.11, 36.69. HRMS (DART) m/z calculated for $C_{11}H_{13}N_2^+$ (M$^+$) 173.10732, found 173.10709.

1-Benzyl-2,3-dimethylimidazolium bromide (2b)

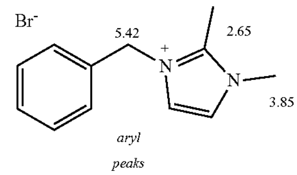

Following general procedure B, 1,2-dimethyl imidazole (2.00 g, 20.8 mmol) was treated with benzyl bromide (3.0 ml, 25 mmol) in acetonitrile (100 ml). The product was recrystallized from chloroform to give 2b (3.05 g, 55%) as a white powder. $^1$H NMR (600 MHz, $CD_3OD$): δ 7.53 (m, 2H), 7.45-7.41 (m, 2H), 7.41-7.37 (m, J=7.3 Hz, 1H), 7.36-7.33 (d, J=7.6 Hz, 2H), 5.42 (s, 2H), 3.85 (s, 3H), 2.65 (s, 3H). $^{13}$C NMR (126 MHz, $CD_3OD$): δ 146.06, 135.18, 130.25, 129.84, 129.11, 123.77, 122.43, 52.66, 35.96, 10.58. HRMS (DART) m/z calculated for $C_{12}H_{15}N_2^+$ (M$^+$) 187.12298, found 187.12293.

1-Ethyl-2,3-dimethylimidazolium iodide (2c)

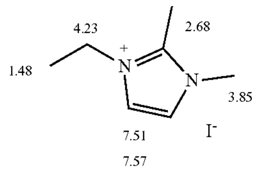

Following general procedure B, 1,2-dimethyl imidazole (2.00 g, 20.8 mmol) was treated with ethyl iodide (2.0 ml, 25 mmol) in acetonitrile (100 ml). The product was dissolved in chloroform and purified via precipitation into tetrahydrofuran to give 2c (5.01 g, 96%) as a white powder. $^1$H NMR (600 MHz, $CD_3OD$): δ 7.57 (d, J=2.1 Hz, 1H), 7.51 (d, J=2.1 Hz, 1H), 4.23 (q, J=7.3 Hz, 2H), 3.85 (s, 3H), 2.68 (s, 3H), 1.48 (t, J=7.3 Hz, 3H). $^{13}$C NMR (126 MHz, $CD_3OD$): δ 145.46, 123.53, 121.45, 44.73, 36.23, 15.61, 10.89. HRMS (DART) m/z calculated for $C_7H_{13}N_2^+$ ($M^+$) 125.10732, found 125.10757.

1-Isopropyl-2,3-dimethylimidazolium iodide (2d)

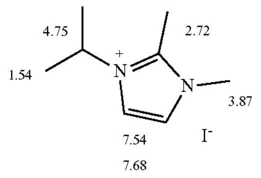

Following general procedure B, 1,2-dimethyl imidazole (2.00 g, 20.8 mmol) was treated with 2-iodopropane (2.3 ml, 23 mmol) in acetonitrile (20 ml). The product was dissolved in chloroform and purified via precipitation into ethyl acetate to give 2d (2.36 g, 50%) as a light beige powder. $^1$H NMR (600 MHz, $CD_3OD$): δ 7.68 (d, J=2.2 Hz, 1H), 7.54 (d, J=2.2 Hz, 1H), 4.75 (hept, J=6.8 Hz, 1H), 3.87 (s, 3H), 2.72 (s, 3H), 1.54 (d, J=6.8 Hz, 6H). $^{13}$C NMR (126 MHz, $CD_3OD$): δ 144.98, 124.02, 118.46, 52.08, 35.91, 22.74, 10.67. HRMS (DART) m/z calculated for $C_8H_{15}N_2^+$ ($M^+$) 139.12298, found 139.12305.

1-n-Butyl-2,3-dimethylimidazolium iodide (2e)

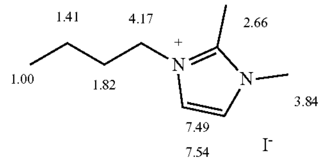

Following general procedure B, 1,2-dimethyl imidazole (2.00 g, 20.8 mmol) was treated with n-butyl iodide (2.6 ml, 23 mmol) in acetonitrile (20 ml). The product was dissolved in chloroform and purified via precipitation into ethyl acetate to give 2e (4.57 g, 78%) as a white powder. $^1$H NMR (600 MHz, $CD_3OD$): δ 7.54 (d, J=2.1 Hz, 1H), 7.49 (d, J=2.1 Hz, 1H), 4.17 (m, 2H), 3.84 (s, 3H), 2.66 (s, 3H), 1.82 (p, J=7.4 Hz, 2H), 1.41 (sext, J=7.4 Hz, 2H), 1.00 (t, J=7.4 Hz, 3H). $^{13}$C NMR (126 MHz, $CD_3OD$): δ 145.65, 123.50, 122.12, 49.35, 36.15, 32.74, 20.48, 13.95, 10.77. HRMS (DART) m/z calculated for $C_9H_{17}N_2^+$ ($M^+$) 153.13863, found 153.13876.

1-Benzyl-2-(2,6-dimethylphenyl)-3,4,5-trimethylimidazolium iodide (3a)

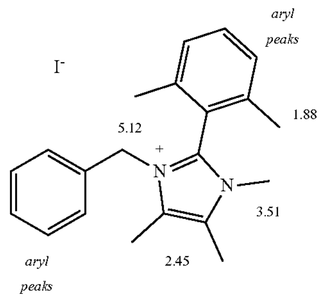

Following general procedure B, IM-3a (0.400 g, 1.38 mmol) was treated with methyl iodide (0.90 ml, 1.5 mmol) in acetonitrile (1.5 ml). The product was dissolved in chloroform and purified via precipitation into ethyl acetate to give 3a (0.382 g, 72%) as a off-white powder. $^1$H NMR (600 MHz, $CD_3OD$): δ 7.52 (t, J=7.7 Hz, 1H), 7.34-7.21 (m, 5H), 6.93 (d, J=7.4 Hz, 2H), 5.12 (s, 2H), 3.51 (s, 3H), 2.47-2.44 (m, 6H), 1.88 (s, 6H). $^{13}$C NMR (126 MHz, $CD_3OD$): δ 144.55, 140.88, 134.83, 133.96, 130.09, 129.70*, 129.50, 128.50, 128.45, 122.52, 50.54, 32.93, 19.69, 9.56, 9.14. HRMS (DART) m/z calculated for $C_{21}H_{25}N_2^+$ ($M^+$) 305.20123, found 305.20134.

1-Benzyl-3,4,5-trimethyl-2-phenylimidazolium iodide (3b)

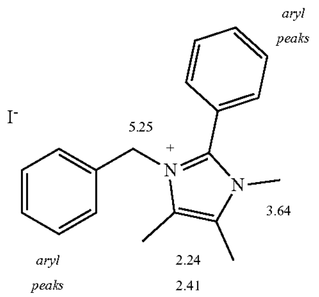

Following general procedure B, IM-3b (2.54 g, 9.68 mmol) was treated with methyl iodide (0.70 ml, 12 mmol) in acetonitrile (7 ml). The product was dissolved in chloroform and purified via precipitation into ether to give 3b (1.74 g, 50%) as an off-white powder. $^1$H NMR (600 MHz, $CD_3OD$): δ 7.74-7.69 (t, J=7.6 Hz, 1H), 7.63 (t, J=7.6 Hz, 2H), 7.61-7.57 (d, J=7.6 Hz, 2H), 7.37-7.28 (m, 3H), 7.07-7.02 (d, J=7.6 Hz, 2H), 5.25 (s, 2H), 3.64 (s, 3H), 2.41 (s, 3H), 2.24 (s, 3H). $^{13}$C NMR (126 MHz, $CD_3OD$): δ 145.24, 135.44, 133.65, 131.76, 130.78, 130.21, 129.33, 129.30, 127.95, 127.33, 123.41, 50.35, 34.00, 9.14, 9.08. HRMS (DART) m/z calculated for $C_{19}H_{21}N_2^+$ ($M^+$) 277.16993, found 277.17009.

1-Benzyl-2-isopropyl-3,4,5-trimethylimidazolium iodide (3c)

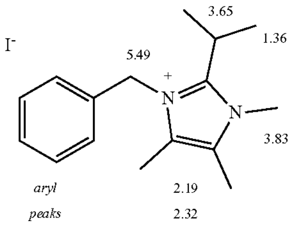

Following general procedure B, IM-3c (1.07 g, 4.69 mmol) was treated with methyl iodide (0.32 ml, 5.2 mmol) in acetonitrile (5 ml). The product was dissolved in chloroform and purified via precipitation into ether to give 3c (1.58 g, 91%) as an orange solid. $^{1}H$ NMR (600 MHz, $CD_3OD$): δ 7.41 (t, J=7.6 Hz, 2H), 7.37-7.32 (t, J=7.6 Hz, 1H), 7.13-7.08 (d, J=7.6 Hz, 2H), 5.49 (s, 2H), 3.83 (s, 3H), 3.65 (hept, J=7.3 Hz, 1H), 2.32 (s, 3H), 2.19 (s, 3H), 1.36 (d, J=7.3 Hz, 6H). $^{13}C$ NMR (126 MHz, $CD_3OD$): δ149.98, 135.89, 130.33, 129.35, 128.79, 127.23, 126.97, 49.49, 33.60, 26.62, 19.13, 8.91, 8.90. HRMS (DART) m z calculated for $C_{16}H_{23}N_2^+$ ($M^+$) 243.18558, found 243.18580.

1-Benzyl-2,3,4,5-tetramethylimidazolium bromide (3d)

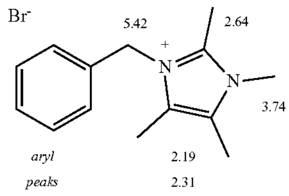

Following general procedure B, 1,2,4,5-tetramethylimidazole (2.00 g, 16.1 mmol) was treated with benzyl bromide (1.9 ml, 16 mmol) in acetonitrile (10 ml). The product was dissolved in chloroform and purified via precipitation into ether to give 3d (3.60 g, 76%) as an off-white powder. $^{1}H$ NMR (600 MHz, $CD_3OD$): δ 7.40 (t, J=7.7 Hz, 2H), 7.37-7.33 (t, J=7.6 Hz, 1H), 7.19-7.14 (d, J=7.6 Hz, 2H), 5.42 (s, 2H), 3.74 (s, 3H), 2.64 (s, 3H), 2.31 (s, 3H), 2.19 (s, 3H). $^{13}C$ NMR (126 MHz, $CD_3OD$): δ 144.40, 135.40, 130.23, 129.27, 127.79, 127.49, 126.60, 49.42, 33.02, 10.98, 8.97, 8.91. HRMS (DART) m/z calculated for $C_4H_{19}N_2^+$ ($M^+$) 215.15428, found 215.1548.

1-Benzyl-2-(2,6-dimethylphenyl)-3-methyl-4,5-diphenylimidazolium bromide (4a)

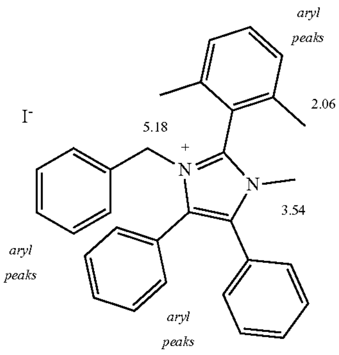

Following general procedure B, IM-4a (0.350 g, 0.844 mmol) was treated with methyl iodide (0.06 ml, 0.9 mmol) in acetonitrile (1.2 ml). The product was dissolved in chloroform and purified via precipitation into ether to give 4a (0.096 g, 22%) as a white powder. $^{1}H$ NMR (500 MHz, $CD_3OD$): δ 7.64-7.44 (m, 11H), 7.35 (d, J=7.7 Hz, 2H), 7.24 (t, J=7.6 Hz, 1H), 7.15 (t, J=7.6 Hz, 2H), 6.66 (d, J=7.7 Hz, 2H), 5.18 (s, 2H), 3.54 (s, 3H), 2.06 (s, 6H). $^{13}C$ NMR (126 MHz, $CD_3OD$): δ 146.19, 140.90, 134.58, 134.37, 134.35, 133.87, 132.68, 132.15, 131.76, 131.57, 130.47, 130.19, 129.94*, 129.89, 129.23, 126.75, 126.43, 122.38, 51.29, 34.14, 19.66. HRMS (DART) m/z calculated for $C_{23}H_{21}N_2^+$ ($M^+$) 325.16993, found 325.16996.

1-Benzyl-3-methyl-2,4,5-triphenylimidazolium bromide (4b)

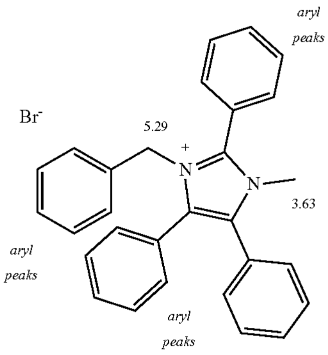

Following general procedure B, IM-4b (0.880 g, 2.84 mmol) was treated with benzyl bromide (0.40 ml, 3.1 mmol) in acetonitrile (10 ml). The product was dissolved in chloroform and purified via precipitation into ether to give 4b (0.567 g, 41%) as an off-white powder. $^{1}H$ NMR (600 MHz, $CD_3OD$): δ 7.83 (d, J=7.6 Hz, 2H), 7.78-7.74 (t, J=7.6 Hz, 1H), 7.70 (t, J=7.6 Hz, 2H), 7.53 (dm, J=7.6 Hz, 2H), 7.50-7.40 (m, 4H), 7.37 (m, 4H), 7.23-7.12 (m, 3H), 6.81-6.75 (m, 2H), 5.29 (s, 2H), 3.63 (s, 3H). $^{13}C$ NMR (126 MHz, $CD_3OD$): δ 146.40, 135.36, 134.32, 133.88, 133.33, 132.31, 132.18, 131.92, 131.32*, 130.87, 130.02, 129.98, 129.79, 129.25, 127.95, 127.00, 126.84, 123.49, 51.25, 35.24. HRMS (DART) m z calculated for $C_{29}H_{25}N_2^+$ ($M^+$) 401.20123, found 401.20079.

1-Benzyl-2-isopropyl-3-methyl-4,5-diphenylimidazolium iodide (4c)

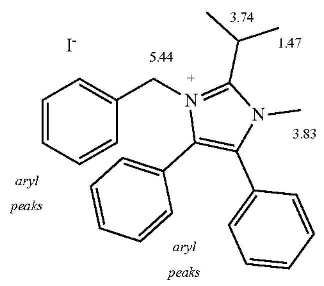

Following general procedure B, IM-4c (1.00 g, 2.89 mmol) was treated with methyl iodide (0.19 ml, 3.1 mmol) in acetonitrile (5 ml). The product was dissolved in chloroform and purified via precipitation into ether to give 4c (1.06 g, 84%) as a pale yellow powder. $^1H$ NMR (600 MHz, $CD_3OD$): δ 6 7.54-7.49 (d, J=7.4 Hz, 2H), 7.44 (m, 3H), 7.37 (m, 5H), 7.33-7.28 (m, 3H), 7.12 (d, J=7.4 Hz, 2H), 5.44 (s, 2H), 3.83 (s, 3H), 3.74 (hept, J=7.3 Hz, 1H), 1.47 (d, J=7.3 Hz, 6H). $^{13}C$ NMR (126 MHz, $CD_3OD$): δ 150.82, 135.93, 134.29, 133.00, 132.60, 132.44, 131.27, 131.22, 130.17, 129.88, 129.84, 129.30, 127.41, 127.02, 126.83, 50.43, 35.05, 27.34, 19.18. HRMS (DART) m/z calculated for $C_{26}H_{27}N_2^+$ ($M^+$) 367.21688, found 367.21702.

1-Benzyl-2,3-dimethyl-4,5-diphenylimidazolium iodide (4d)

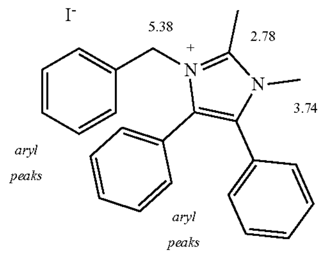

Following general procedure B, IM-4d (0.405 g, 1.25 mmol) was treated with methyl iodide (0.09 ml, 1 mmol) in acetonitrile (1.5 ml). The product was dissolved in chloroform and purified via precipitation into ether to give 4d (0.190 g, 36%) as a white powder. $^1H$ NMR (600 MHz, $CD_3OD$): δ 6 7.50-7.39 (m, 6H), 7.37-7.29 (m, 5H), 7.29-7.25 (dm, J=7.8 Hz, 2H), 7.08 (dm, J=7.5 Hz, 2H), 5.38 (s, 2H), 3.74 (s, 3H), 2.78 (s, 3H). $^{13}C$ NMR (126 MHz, $CD_3OD$): δ 146.00, 135.36, 133.48, 132.71, 132.31, 132.22, 131.34, 131.26, 130.22, 130.02, 129.98, 129.43, 127.65, 126.96, 126.95, 50.28, 34.06, 11.54. HRMS (DART) m/z calculated for $C_{24}H_{23}N_2^+$ ($M^+$) 339.18558, found 339.18559.

1-Benzyl-2-(2,6-dimethylphenyl)-3-ethyl-4,5-diphenylimidazolium bromide (5a)

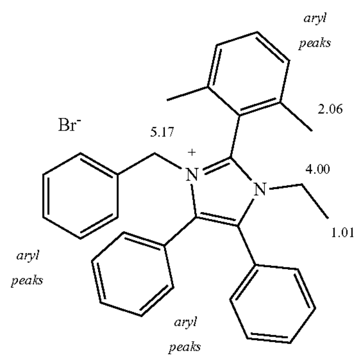

Following general procedure B, IM-5a (0.110 g, 0.312 mmol) was treated with benzyl bromide (0.05 ml, 0.4 mmol) in acetonitrile (1 ml). The product was dissolved in chloroform and purified via precipitation into ether to give 5a (0.080 g, 49%) as a white powder. $^1H$ NMR (600 MHz, $CD_3OD$): δ 7.65-7.45 (m, 11H), 7.36 (d, J=7.7 Hz, 2H), 7.24 (t, J=7.5 Hz, 1H), 7.15 (tm J=7.7 Hz, 2H), 6.64 (d, J=7.7 Hz, 2H), 5.17 (s, 2H), 4.00 (q, J=7.3 Hz, 2H), 2.06 (s, 6H), 1.01 (t, J=7.3 Hz, 3H). $^{13}C$ NMR (126 MHz, $CD_3OD$): δ 145.59, 140.73, 134.58, 134.37, 134.31, 133.87, 132.65, 132.16, 131.74, 131.70, 130.43, 130.37, 130.12, 129.96, 129.89, 129.26, 126.63, 126.61, 122.40, 51.22, 43.49, 19.92, 14.96. HRMS (DART) m/z calculated for $C_{32}H_{31}N_2^+$ ($M^+$) 443.24818, found 443.24856.

1-Benzyl-3-ethyl-2,4,5-triphenylimidazolium iodide (5b)

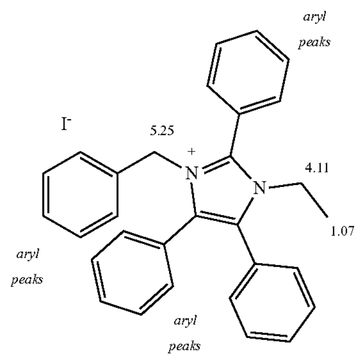

Following general procedure B, IM2-4b (0.825 g, 2.14 mmol) was treated with ethyl iodide (0.19 ml, 2.4 mmol) in acetonitrile (3 ml). The product was dissolved in chloroform and purified via precipitation into ether to give 5b (0.805 g, 76%) as an off-white powder. $^1H$ NMR (600 MHz, $CD_3OD$): δ 7.82-7.74 (m, 3H), 7.70 (m, 2H), 7.58-7.45 (m, 5H), 7.43 (m, 1H), 7.36 (m, 4H), 7.18 (m, 3H), 6.75 (d, J=7.6 Hz, 2H), 5.25 (s, 2H), 4.11 (q, J=7.3 Hz, 2H), 1.07 (t, J=7.3 Hz, 3H). $^{13}C$ NMR (126 MHz, $CD_3OD$): δ 145.84, 135.25, 133.95*, 133.49, 132.41, 132.34, 132.00, 131.51, 131.36, 130.93, 130.14, 129.92, 129.84, 129.30, 128.08, 126.96, 126.87, 123.51, 51.23, 43.73, 15.46. HRMS (DART) m/z calculated for $C_{30}H_{27}N_2^+$ ($M^+$) 415.21688, found 415.21657.

1-Benzyl-3-n-butyl-2-(2,6-dimethylphenyl)-4,5-diphenylimidazolium iodide (6a)

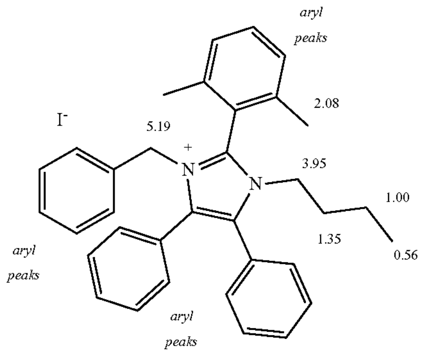

Following general procedure B, IM-4a (0.500 g, 1.21 mmol) was treated with n-butyl iodide (0.15 ml, 1.3 mmol) in acetonitrile (1 ml). The product was dissolved in chloroform and purified via precipitation into ether to give 6a (0.397 g, 60%) as a pale yellow powder. $^1$H NMR (600 MHz, $CD_3OD$): δ 7.63-7.54 (m, 5H), 7.50 (m, 6H), 7.36 (dm, J=7.5 Hz, 2H), 7.23 (tm, J=7.5 Hz, 1H), 7.14 (tm, J=7.6 Hz, 2H), 6.63 (dm, J=7.6 Hz, 2H), 5.19 (s, 2H), 3.97-3.92 (m, 2H), 2.08 (s, 6H), 1.35 (p, J=7.4 Hz, 2H), 1.00 (sext, J=7.4 Hz, 2H), 0.56 (t, J=7.4 Hz, 3H). $^{13}$C NMR (126 MHz, $CD_3OD$): δ 145.70, 140.72, 134.42, 134.35, 134.28, 134.06, 132.69, 132.27, 131.69, 131.66, 130.41, 130.33, 130.13, 129.92, 129.88, 129.25, 126.70, 126.60, 122.40, 51.32, 47.70, 32.17, 20.30, 20.12, 13.22. HRMS (DART) m z calculated for $C_{34}H_{35}N_2^+$ ($M^+$) 471.27948, found 471.27828.

1-Benzyl-3-n-butyl-2,4,5-triphenylimidazolium bromide (6b)

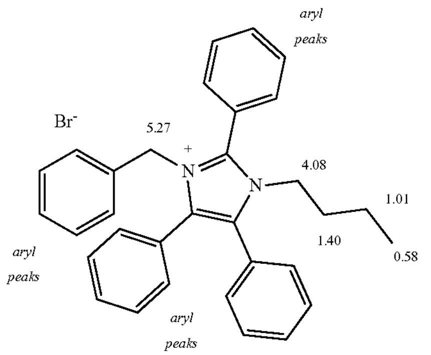

Following general procedure B, IM-6b (1.10 g, 3.12 mmol) was treated with benzyl bromide (0.40 ml, 3.4 mmol) in acetonitrile (3 ml). The product was dissolved in chloroform and purified via precipitation into ether to give 6b (0.527 g, 32%) as a white powder. $^1$H NMR (600 MHz, $CD_3OD$): δ 7.84-7.74 (m, 3H), 7.71 (d, J=6.8 Hz, 2H), 7.55 (dm, J=7.6 Hz, 2H), 7.53-7.46 (m, 3H), 7.42 (m, 1H), 7.40-7.33 (m, 4H), 7.17 (m, 3H), 6.79-6.67 (d, J=7.5 Hz, 2H), 5.27 (s, 2H), 4.08 (m, 2H), 1.40 (p, J=7.4 Hz, 2H), 1.01 (sext, J=7.4 Hz, 2H), 0.58 (t, J=7.4 Hz, 3H). $^{13}$C NMR (126 MHz, $CD_3OD$): δ 146.14, 135.26, 134.01, 133.96, 133.69, 132.29, 132.20, 131.90, 131.54, 131.42, 131.03, 130.23, 130.03, 129.85, 129.37, 128.02, 126.98, 126.82, 123.54, 51.23, 47.90, 32.39, 20.21, 13.29. HRMS (DART) m/z calculated for $C_{32}H_{31}N_2^+$ ($M^+$) 443.24818, found 443.24683.

1,3-Di-n-butyl-2-(2,6-dimethylphenyl)-4,5-dimethylimidazolium iodide (7a)

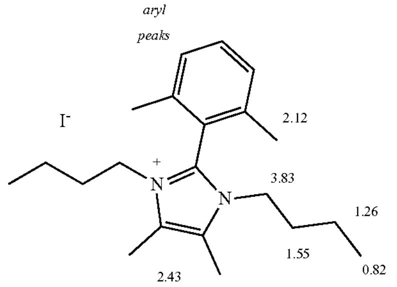

Following general procedure B, IM-7a (0.240 g, 0.937 mmol) was treated with n-butyl iodide (0.13 ml, 1.1 mmol) in acetonitrile (1.5 ml). The product was dissolved in chloroform and purified via precipitation into ether to give 7a (0.366 g, 89%) as a light beige powder. $^1$H NMR (600 MHz, $CD_3OD$): δ 7.57 (t, J=7.7 Hz, 1H), 7.39 (d, J=7.7 Hz, 2H), 3.89-3.75 (m, 4H), 2.43 (s, 6H), 2.12 (s, 6H), 1.59-1.52 (p, J=7.4 Hz, 4H), 1.26 (sext, J=7.4 Hz, 4H), 0.82 (t, J=7.4 Hz, 6H). $^{13}$C NMR (126 MHz, $CD_3OD$): δ 143.30, 140.40, 133.97, 130.02, 128.66, 122.75, 46.91, 32.43, 20.61, 20.09, 13.57, 9.06. HRMS (DART) m z calculated for $C_{21}H_{33}N_2^+$ ($M^+$) 313.26383, found 313.26388.

1,3-Di-n-butyl-4,5-dimethyl-2-phenylimidazolium iodide (7b)

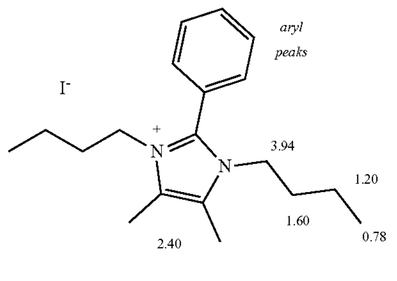

Following general procedure B, IM-7b (0.262 g, 1.15 mmol) was treated with n-butyl iodide (0.15 ml, 1.4 mmol) in acetonitrile (1 ml). The product was dissolved in chloroform and purified via precipitation into ether to give 7b (0.298 g, 63%) as a orange waxy solid. $^1$H NMR (600 MHz, $CD_3OD$): δ 7.80-7.75 (t, J=7.4 Hz 1H), 7.73 (t, J=7.6 Hz, 2H), 7.68-7.65 (d, J=7.6 Hz, 2H), 3.99-3.85 (m, 4H), 2.40 (s, 6H), 1.65-1.56 (p, J=7.4 Hz, 4H), 1.20 (sext, J=7.4 Hz, 4H), 0.78 (t, J=7.4 Hz, 6H). $^{13}$C NMR (126 MHz, $CD_3OD$): δ 144.16, 133.61, 131.93, 130.89, 128.00, 123.85, 79.60, 46.95, 32.70, 20.50, 13.59, 9.04. HRMS (DART) m/z calculated for $C_{19}H_{29}N_2$'($M^+$) 285.23253, found 285.23174.

1,3-Di-n-butyl-2-(2,6-dimethylphenyl)-4,5-diphenylimidazolium iodide (8a)

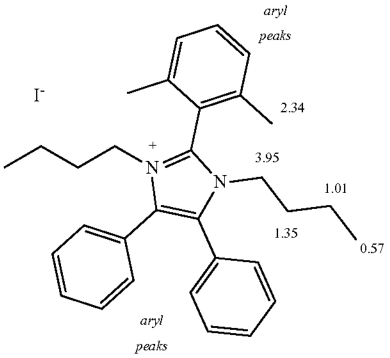

Following general procedure B, IM-8a (1.86 g, 4.89 mmol) was treated with n-butyl iodide (0.61 ml, 5.4 mmol) in acetonitrile (5 ml). The product was dissolved in chloroform and purified via precipitation into ether to give 8a (1.27 g, 46%) as an pale beige powder. $^1H$ NMR (600 MHz, $CD_3OD$): δ 7.63 (t, J=7.7 Hz, 1H), 7.57-7.54 (m, 4H), 7.54-7.44 (m, 8H), 3.99-3.89 (m, 4H), 2.34 (s, 6H), 1.40-1.29 (p, J=7.4 Hz, 4H), 1.01 (sext, J=7.4 Hz, 4H), 0.57 (t, J=7.4 Hz, 6H). $^{13}C$ NMR (126 MHz, $CD_3OD$): δ 144.95, 140.54, 134.31, 134.06, 132.26, 131.61, 130.29, 130.23, 126.76, 122.42, 47.65, 32.22, 20.39, 20.32, 13.24. HRMS (DART) m/z calculated for $C_{31}H_{37}N_2^+$ ($M^+$) 437.29513, found 437.29517.

1,3-Di-n-butyl-2,4,5-triphenylimidazolium iodide (8b)

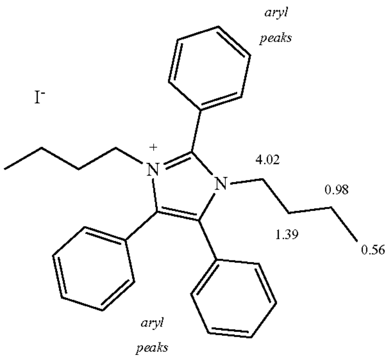

Following general procedure B, IM-6b (3.74 g, 10.6 mmol) was treated with n-butyl iodide (1.8 ml, 16 mmol) in acetonitrile (10 ml). The product was dissolved in chloroform and purified via precipitation into ether to give 8b (3.50 g, 61%) as a white powder. $^1H$ NMR (500 MHz, $CD_3OD$): δ 8.02 (d, J=7.6 Hz, 2H), 7.79 (m, 3H), 7.63-7.56 (d, J=7.3 Hz, 4H), 7.50-7.40 (m, 6H), 4.02 (m, 4H), 1.39 (p, J=7.4 Hz, 4H), 0.98 (sext, J=7.4 Hz, 4H), 0.56 (t, J=7.4 Hz, 6H). $^{13}C$ NMR (126 MHz, $CD_3OD$): δ 145.32, 133.93, 133.36, 132.36, 132.18, 131.39, 131.00, 130.08, 127.19, 123.79, 47.73, 32.47, 20.27, 13.30. HRMS (DART) m/z calculated for $C_{29}H_{33}N_2^+$ ($M^+$) 409.26383, found 409.26371.

General Procedure C: Model Compound Study Procedure

Stock solutions of the basic methanol were prepared by dissolving KOH (1M, 2M, or 5M) and 3-(Trimethylsilyl)-1-propanesulfonic acid sodium salt (0.025M) in $CD_3OH$. The model compound (0.05M for 1M KOH and 0.03M for 2M and 5M KOH) was dissolved in the methanol solution (0.5 mL) and passed through a glass wool plug into an NMR tube. The NMR tube was flame sealed and analyzed by $^1H$ NMR spectroscopy for the initial time point. Integration of a selected signal in the model compound relative to a signal related to 3-(Trimethylsilyl)-1-propanesulfonic acid sodium salt provided the initial quantity of model compound. The tube was heated in an oil bath at 80° C. At specified time points, every 5 days, the tubes were removed, cooled to room temperature and analyzed by $^1H$ NMR spectroscopy in order to determine the quantity of model compound remaining.

Results

Stability results for the tested compounds are summarized in Table I:

TABLE I

| Model Compound | [KOH] | Cation remaining (%)[b] 5d | 10d | 15d | 20d | 25d | 30d |
|---|---|---|---|---|---|---|---|
| 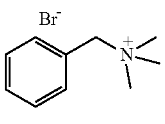 1 | 1M | 75 | 56 | 29 | 19 | 15 | 11 |
| | 2M[c] | 45 | 28 | n.d.[d] | 8 | n.d. | <1 |
| | 5M[c,e] | 5 | n.d. | n.d. | <1 | n.d. | n.d. |
| 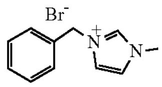 2a | 1M | 2 | <1 | n.d. | n.d. | n.d. | n.d. |
| | 2M[c] | <1 | n d. | n.d. | n.d. | n.d. | n.d. |
| | 5M[c] | <1 | n.d. | n.d. | n.d. | n.d. | n.d. |
| 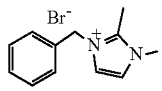 2b | 1M | 77 | 64 | 56 | 49 | 44 | 36 |
| | 2M[c,e] | 28 | 5 | n.d. | n.d. | n.d. | n.d. |
| | 5M[c,e] | <1 | n.d. | n.d. | n.d. | n.d. | n.d. |
| 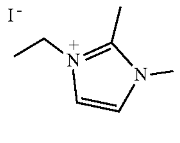 2c | 1M | 95 | 91 | 86 | n.d. | 72 | 71 |
| | 2M[c,e] | 43 | 29 | 20 | 13 | 11 | 8 |
| | 5M[c,e] | <1 | n.d. | n.d. | n.d. | n.d. | n.d. |
| 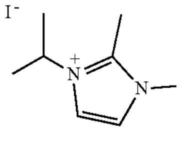 2d | 1M | 98 | 96 | 94 | n.d. | 97 | 89 |
| | 2M[c] | 72 | 63 | 56 | 46 | 41 | 37 |
| | 5M[c,e] | 1 | n.d. | n.d. | n.d. | n.d. | n.d. |

TABLE I-continued
| Model Compound | [KOH] | Cation remaining (%)[b] 5d | 10d | 15d | 20d | 25d | 30d |
|---|---|---|---|---|---|---|---|
| 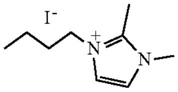 2e | 1M | 95 | 87 | 85 | 80 | 77 | 75 |
| | 2M[c] | 68 | 56 | 45 | 34 | 29 | 27 |
| | 5M[c,e] | <1 | n.d. | n.d. | n.d. | n.d. | n.d. |
| 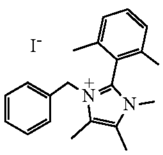 3a | 1M | n.d. | >99 | >99 | n.d. | >99 | >99 |
| | 2M[c] | >99 | 99 | 98 | 99 | n.d. | 99 |
| | 5M[c] | 99 | 99 | 98 | 99 | 97 | 96 |
| 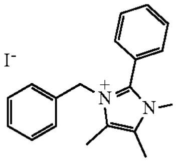 3b | 1M | >99 | >99 | >99 | 99 | >99 | >99 |
| | 2M[c] | 99 | 98 | 97 | 96 | 97 | 95 |
| | 5M[c] | 81 | 71 | 61 | 54 | 49 | 43 |
| 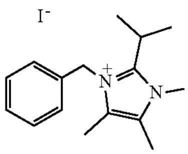 3c | 1M | 99 | 97 | 97 | 96 | 96 | 95 |
| 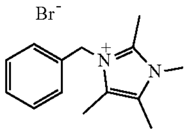 3d | 1M | 98 | 94 | 92 | 91 | 90 | 87 |
| 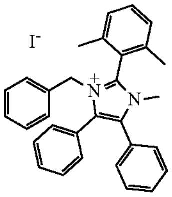 4a | 1M | 97 | 95 | 92 | 91 | 90 | 87 |
| | 2M[c] | 93 | 87 | 77 | n.d. | 70[f] | 66 |
| | 5M[c] | 70 | 52 | 39 | 31 | 21 | 18 |
TABLE I-continued
| Model Compound | [KOH] | Cation remaining (%)[b] 5d | 10d | 15d | 20d | 25d | 30d |
|---|---|---|---|---|---|---|---|
| 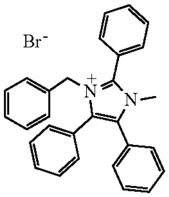 4b | 1M | 97 | 95 | 94 | 93 | 92 | 91 |
| | 2M[c] | 98 | 94 | 89 | 82 | 76 | 69 |
| | 5M[c] | 1 | n.d. | n.d. | n.d. | n.d. | n.d. |
| 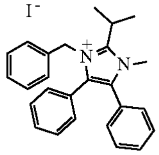 4c | 1M | 98 | 94 | 91 | 89 | 86 | 82 |
| 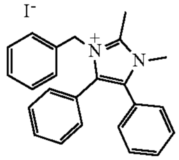 4d | 1M | 95 | 91 | 88 | 86 | 85 | 80 |
| 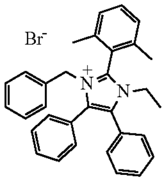 5a | 1M | 97 | 97 | 95 | 94 | 93 | 91 |
| | 2M[c] | 97 | 93 | 91 | 88 | 85 | 84 |
| | 5M[c] | 80 | 70 | 55 | 46 | 42 | 37 |
| 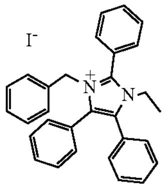 5b | 1M | 99 | 98 | 98 | 97 | 95 | 94 |
| | 2M[c] | 96 | 94 | 92 | 91 | 89 | 86 |
| | 5M[c] | 29 | 9 | 4 | 2 | n.d. | n.d. |
| 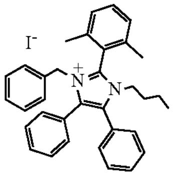 6a | 1M | 98 | 98 | n.d. | 96 | 95 | 95 |
| | 2M[c] | 98 | 95 | 92 | 89 | 87 | 86 |
| | 5M[c] | 80 | 69 | 61 | 46 | 39 | 35 |

TABLE I-continued

| Model Compound | [KOH] | Cation remaining (%)[b] | | | | | |
|---|---|---|---|---|---|---|---|
| | | 5d | 10d | 15d | 20d | 25d | 30d |
| 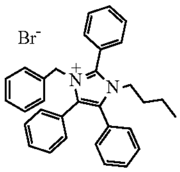 | 1M | n.d. | 99 | 98 | 97 | 97 | 96 |
| | 2M[c] | 96 | 94 | 92 | 90 | 88 | 86 |
| 6b | 5M[c] | 44 | 30 | 19 | 11 | 8 | 5 |
| 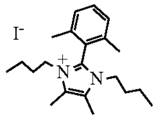 | 1M | >99 | >99 | 99 | >99 | 99 | >99 |
| | 2M[c] | >99 | 99 | 98 | 99 | >99 | >99 |
| 7a | 5M[c] | >99 | >99 | >99 | >99 | >99 | >99 |
| 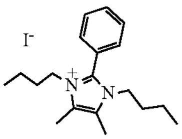 | 1M | >99 | >99 | >99 | >99 | 99 | >99 |
| | 2M[c] | 99 | 96 | 97 | 96 | 97 | 97 |
| 7b | 5M[c] | >99 | >99 | 96 | 96 | 96 | 93 |
| 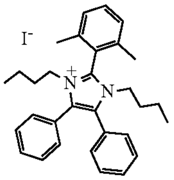 | 1M | >99 | >99 | 99 | >99 | >99 | >99 |
| | 2M[c] | 99 | >99 | >99 | 99 | >99 | >99 |
| 8a | 5M[c] | >99 | >99 | >99 | >99 | >99 | >99 |
| 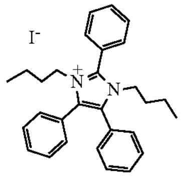 | 1M | >99 | >99 | >99 | >99 | >99 | >99 |
| | 2M[c] | 99 | >99 | >99 | >99 | >99 | 99 |
| 8b | 5M[c] | 96 | 92 | 90 | 86 | 85 | 82 |

[a]Reaction Conditions: [ImX]:[KOH] = 1:20, 1:67, 1:167 for 1M, 2M, and 5M KOH experiments, respectively and at 80° C.
[b]Percent of cation remaining, determined by $^1$H NMR spectroscopy relative to an internal standard, 3-(trimethylsilyl)-1-propanesulfonic acid sodium salt.
[c]The imidazolium concentration was reduced from 0.05M to 0.03M at higher base concentrations due to reduced solubility of the organic salt.
[d]Not determined.
[e]Analyses were performed at time intervals less than 5 days for samples that were anticipated to have low stability.
[f]Analysis performed after 17 days.

Synthesis of Imidazolium Cation Functionalized Monomers

Imidazolium functionalized monomers according to formulas (IIA), (IIB), and (IIC) suitable for ROMP were prepared as follows. While prepared exemplary compounds are shown, persons having ordinarily skill in the art will readily appreciate that the depicted methods and variations thereof can be used to prepare additional compounds, both according to formulas (IIA)-(IIC), and otherwise (e.g., having different $R^1$ substituents, and, when anticipating ROMP, optionally having a different non-cyclooctene strained-ring).

Monomer Synthesis for Exemplary Embodiments of Formula (IIA):

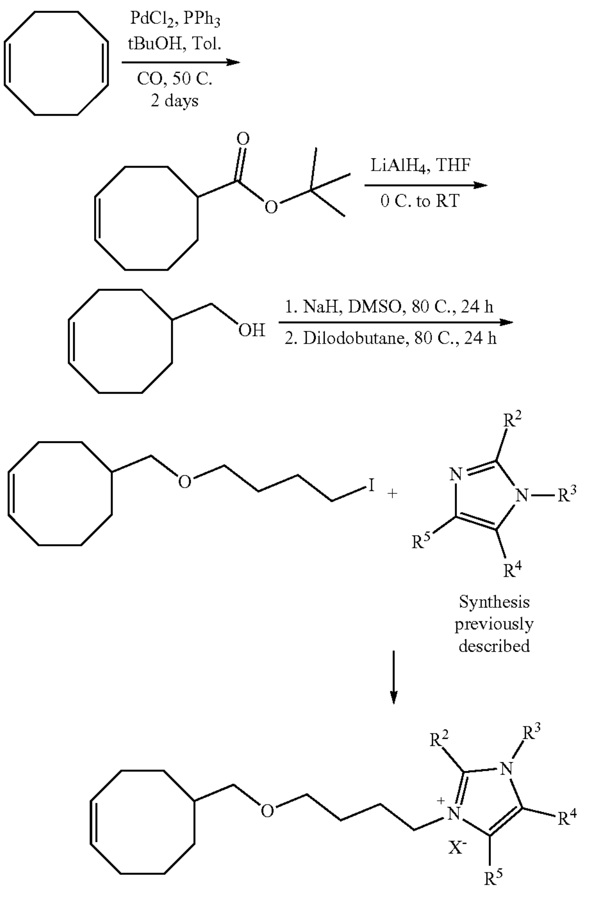

(IIA)

$R^2$ = Ph
$R^3$ = $^n$Bu
$R^4$ and $R^5$ = Ph

Monomer Synthesis for Exemplary Embodiments of Formula (IIB):

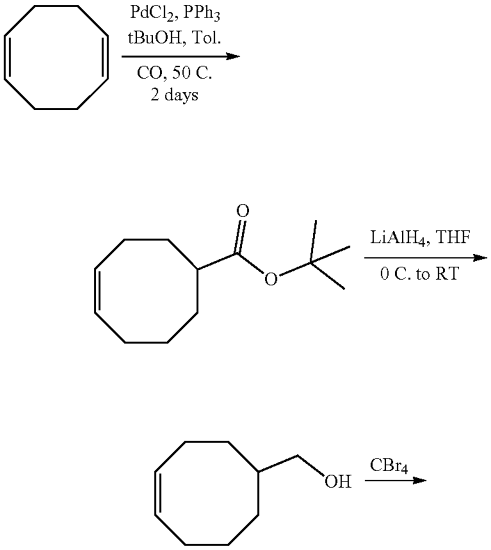

-continued

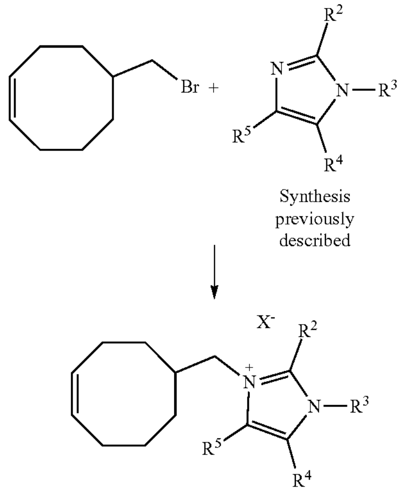

(IIB)

$R^2$ = Me
$R^3$ = Me
$R^4$ and $R^5$ = Me

Monomer Synthesis for Exemplary Embodiments of Formula (IIC):

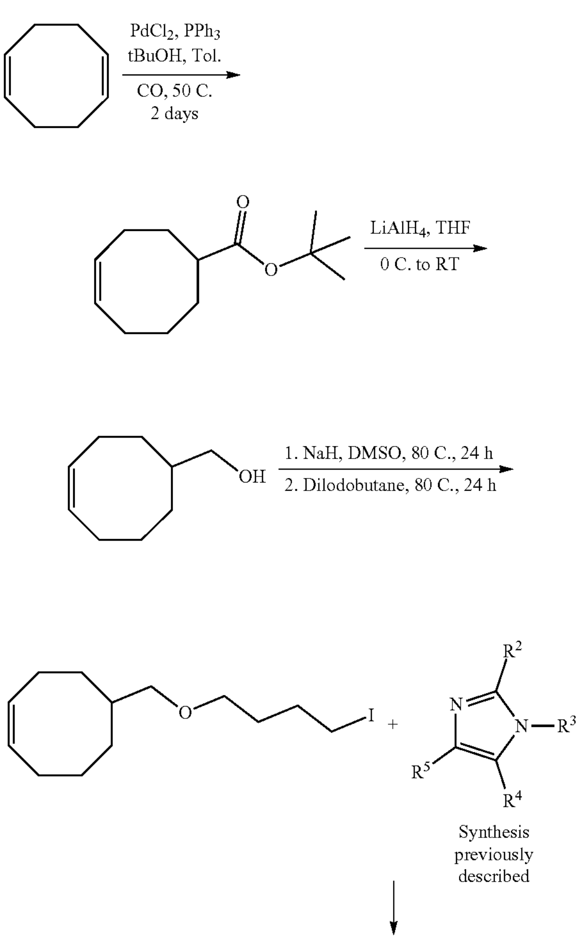

-continued

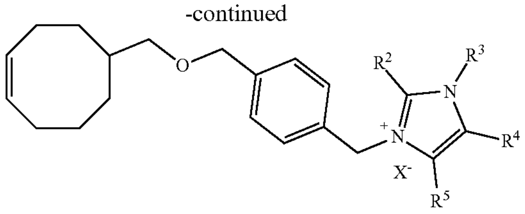

(IIC)

$R^2$ = Ph; 2,6-$(CH_3)_2$Ph; 2,4,6-$(CH_3)_2$Ph, 2,4,6-$(^iPr)_3$Ph
$R^3$ = Me
$R^4$ and $R^5$ = Ph Synthesis of Polymers Examples of embodiments of imidazolium functionalized polymers according to the invention were prepared as follows:

Synthesis of Exemplary Polymers from Monomers of Formula (IIC):

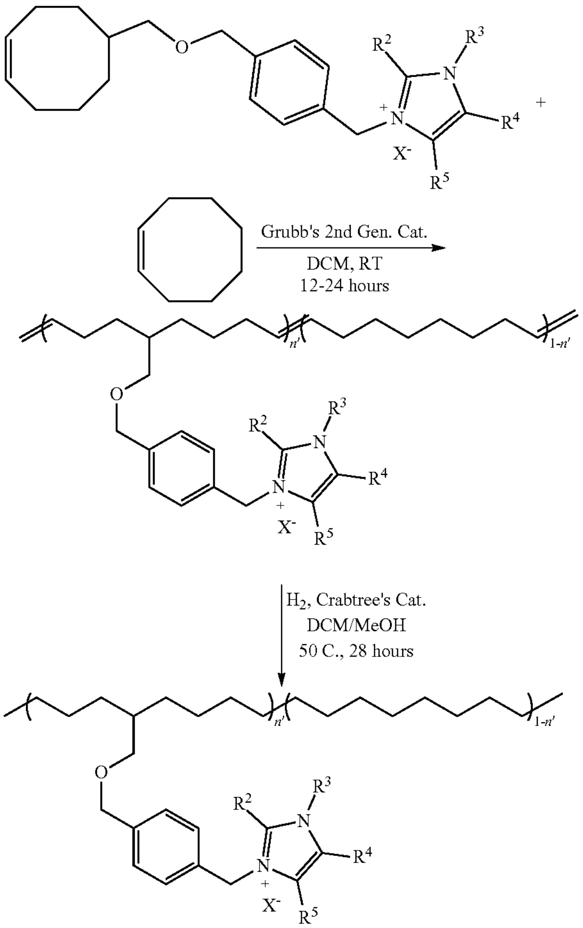

$R^2$ = Ph; 2,6-$(CH_3)_2$Ph; 2,4,6-$(CH_3)_2$Ph, 2,4,6-$(^iPr)_3$Ph
$R^3$ = Me
$R^4$ and $R^5$ = Ph In general, polymerization may be accomplished by ROMP as discussed above. Either an imidazolium monomer may be polymerized as a homopolymer, or it may be copolymerized with a monomer precursor for an HRU. Monomer precursors of HRUs in ROMP are well-known in the art. In certain embodiments of the instant invention, the monomer can be an aliphatic ($C_1$-$C_{20}$)hydrocarbon containing at least one double bond in a carbocycle. Polymers can be created in which all repeating units are IRUs; polymers can be created in which there are IRUs and HRUs; and polymers can be created in which some of the HRUs are cross-linking HRUs. To make the class of cross-linked polymers in which the cross link is through the HRU, a monomer may be added in which the aliphatic hydrocarbon contains a double bond in each of two carbocycles:

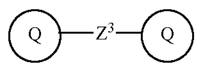

($Z^3$ is a ($C_1$-$C_{20}$)hydrocarbon).

Other methods of polymerization may also be employed to prepare the inventive polymers having imidazolium cations appended to polymer backbones. In addition to ring-opening metathesis polymerization (ROMP) of strained cyclic olefins, controlled radical polymerization, such as atom transfer radical polymerization (ATRP) or reversible addition fragmentation polymerization (RAFT), produce polycations from pre-functionalized cationic monomers. Polymerization of α-olefins by a transition metal coordination complex is another possibility for monomers based on imidazolium cations, because the bulky substituents on the heteroatomic ring may prevent deleterious side reactions of the catalyst with the monomer. Alternatively, imidazolium cations can be easily attached to polymer backbones that contain electrophiles via a post polymerization modification approach. For example, imidazoles will react with benzylic halides or alkyl halides that are present in existing polymers to result in imidazoliums directly attached to the polymer. Polymers with reactive electrophilic sites may be synthesized via step-growth polymerization, radical polymerization or transition metal catalyzed coordination-insertion polymerization routes.

The following is an example of an embodiment wherein polymerization was carried out via polyolefin metathesis:

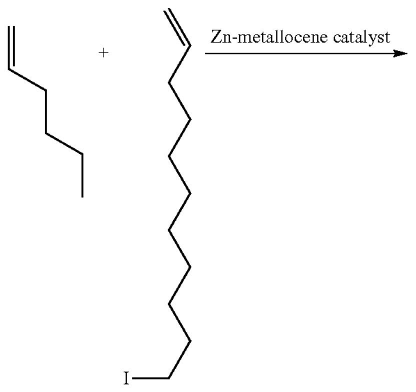

-continued

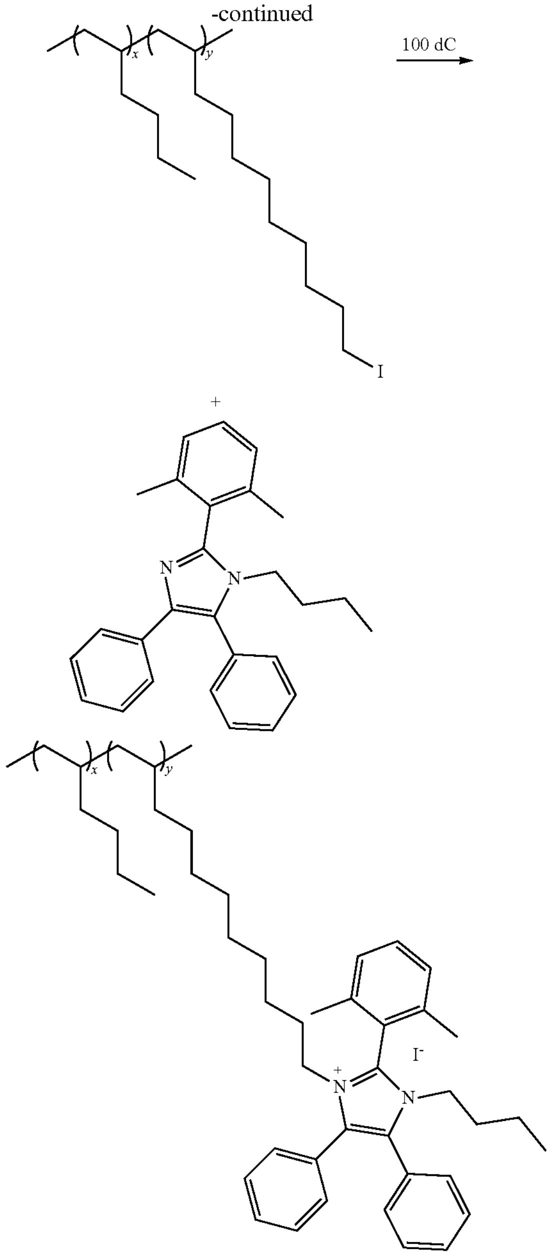

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of compromise, such as "comprises" and "comprising"), "have" (and any form of have, such as "has," and "having"), "include" (and any form of include, such as "includes" and "including"), "contain" (and any form contain, such as "contains" and "containing"), and any other grammatical variant thereof, are open-ended linking verbs. As a result, a method or composition of matter/article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features.

As used herein, the terms "comprising," "has," "including," "containing," and other grammatical variants thereof encompass the terms "consisting of" and "consisting essentially of."

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

All publications cited in this specification are herein incorporated by reference as if each individual publication were specifically and individually indicated to be incorporated by reference herein as though fully set forth.

Subject matter incorporated by reference is not considered to be an alternative to any claim limitations, unless otherwise explicitly indicated.

Where one or more ranges are referred to throughout this specification, each range is intended to be a shorthand format for presenting information, where the range is understood to encompass each discrete point within the range as if the same were fully set forth herein.

While several aspects and embodiments of the present invention have been described and depicted herein, alternative aspects and embodiments may be affected by those skilled in the art to accomplish the same objectives. Accordingly, this disclosure and the appended claims are intended to cover all such further and alternative aspects and embodiments as fall within the true spirit and scope of the invention.

The invention claimed is:

1. A compound of formula (I) or (II):

(I)

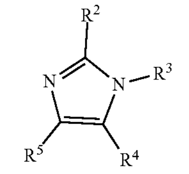

(II)

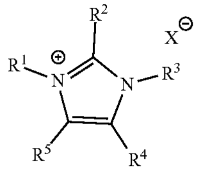

wherein:

$R^1$ is selected from $C_2$-$C_{16}$ hydrocarbyl, wherein one carbon atom of the $C_2$-$C_{16}$ hydrocarbyl may optionally be replaced by O;

$R^2$ is a moiety of formula;

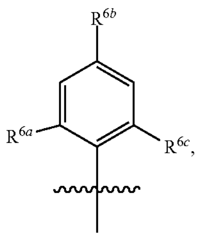

wherein:

represents the point of attachment to the imidazole or imidazolium ring; and $R^{6a}$, $R^{6b}$, and $R^{6c}$ are individually selected from $C_1$-$C_3$ alkyl;

$R^3$ is selected from $C_2$-$C_{16}$ hydrocarbyl;

$R^4$ and $R^5$ are individually selected from $C_1$-$C_{16}$ hydrocarbyl, or, taken together, $R^4$ and $R^5$, together with the carbon atoms to which they attached, form a ring selected from benzene, cyclooctene and norbornene; and $X^-$ is a counterion.

2. A compound according to claim 1 of formula (I), wherein $R^3$ is selected from $C_2$-$C_{12}$ hydrocarbyl, or of formula (II), wherein $R^1$ and $R^3$ are independently selected from $C_2$-$C_{12}$ hydrocarbyl.

3. A compound according to claim 1 of formula (I), wherein $R^3$ is selected from $C_2$-$C_7$ hydrocarbyl, or of formula (II), wherein $R^1$ and $R^3$ are independently selected from $C_2$-$C_7$ hydrocarbyl.

4. A compound according to claim 1 of formula (I), wherein $R^3$ is selected from $C_2$-$C_4$ alkyl and benzyl, or of formula (II), wherein $R^1$ and $R^3$ are independently selected from $C_2$-$C_4$ alkyl and benzyl.

5. A compound according to claim 1, wherein at least two of $R^{6a}$, $R^{6b}$, and $R^{6c}$ are individually selected from methyl and isopropyl.

6. A compound according to claim 1, wherein $R^4$ and $R^5$ are individually selected from phenyl and $C_1$-$C_3$ alkyl.

7. A compound according to claim 1, wherein $X^-$ is selected from hydroxide, halide, bicarbonate, carbonate, nitrate, cyanide, carboxylate and alkoxide.

8. A compound according to claim 1, the compound having an alkaline stability of greater than or equal to 95% cation remaining after 30 days in 5M KOH/$CD_3OH$ at 80° C.

9. A compound according to claim 1 of formula (II), wherein $R^1$ is:

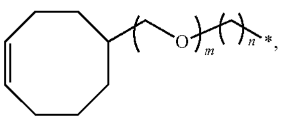

wherein:

* represents the point of attachment to the nitrogen atom at position 1 of the imidazolium ring;

m is 0 or 1; and n is 1-8, provided that the sum of m+n does not exceed 8.

10. A compound according to claim 1, wherein the compound is a compound of formula (II):

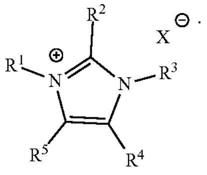

(II)

11. A compound according to claim 5, wherein the compound is a compound of formula (II):

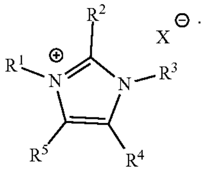

(II)

12. A compound according to claim 9, wherein the compound is a compound of formula (II):

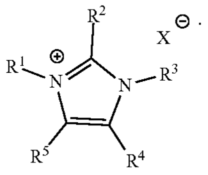

(II)

13. A compound according to claim 1, wherein $R^4$ and $R^5$, together with the carbon atoms to which they are attached, form benzene.

14. A compound according to claim 1, wherein $R^4$ and $R^5$, together with the carbon atoms to which they are attached, form cyclooctene.

15. A compound according to claim 1, wherein $R^4$ and $R^5$, together with the carbon atoms to which they are attached, form norbornene.

16. A compound according to claim 1, wherein $R^3$ is benzyl.

* * * * *